(12) United States Patent
Hu et al.

(10) Patent No.: US 11,578,346 B2
(45) Date of Patent: Feb. 14, 2023

(54) TRANSFORMANT FOR PRODUCING 2,5-FURANDICARBOXYLIC ACID AND PREPARATION METHOD FOR 2,5-FURANDICARBOXYLIC ACID

(71) Applicants: National Tsing Hua University, Hsinchu (TW); Chang Chun Plastics Co., Ltd., Taipei (TW); Chang Chun Petrochemical Co., Ltd., Taipei (TW); Dairen Chemical Corp., Taipei (TW)

(72) Inventors: Yu-Chen Hu, Hsinchu (TW); Nam Ngoc Pham, Hsinchu (TW)

(73) Assignees: National Tsing Hua University, Hsinchu (TW); Chang Chun Plastics Co., Ltd., Taipei (TW); Chang Chun Petrochemical Co., Ltd., Taipei (TW); Dairen Chemical Corp., Taipei (TW)

( * ) Notice: Subject to any disclaimer, the term of this patent is extended or adjusted under 35 U.S.C. 154(b) by 261 days.

(21) Appl. No.: 17/108,069

(22) Filed: Dec. 1, 2020

(65) Prior Publication Data
US 2021/0189443 A1    Jun. 24, 2021

(30) Foreign Application Priority Data
Dec. 23, 2019 (TW) ................................ 108147257

(51) Int. Cl.
| | |
|---|---|
| *C12N 9/22* | (2006.01) |
| *C12P 17/04* | (2006.01) |
| *C12N 9/04* | (2006.01) |
| *C12N 15/78* | (2006.01) |

(52) U.S. Cl.
CPC ............ *C12P 17/04* (2013.01); *C12N 9/0006* (2013.01); *C12N 15/78* (2013.01); *C12Y 101/03* (2013.01)

(58) Field of Classification Search
CPC .................................. C12N 7/22; C12N 15/78
See application file for complete search history.

(56) References Cited

U.S. PATENT DOCUMENTS 9,828,616 B2   11/2017   Wierckx et al.

OTHER PUBLICATIONS

Pham, Nam Ngoc, et al., "Engineering Stable Pseudomonas putida S12 by CRISPR for 2,5-Furandicarboxylic Acid (FDCA) Production", ACS Synthetic Biology, published on Apr. 16, 2020, vol. 9, issue 5, pp. 1138-1149, published by American Chemical Society, United States.

Cook et al., "Genetic tools for reliable gene expression and recombineering in Pseudomonas putida", Journal of Industrial Microbiology & Biotechnology, published on Jan. 3, 2018, vol. 45, issue 7, pp. 517-527, published by Society for Industrial Microbiology, United States.

Sajid et al., "Production of 2,5-furandicarboxylic acid (FDCA) from 5-hydroxymethylfurfural (HMF): recent progress focusing on the chemical-catalytic routes", Green Chemistry, published on Oct. 24, 2018, vol. 20, issue 24, pp. 5427-5453, published by the Royal Society of Chemistry, United Kingdom.

*Primary Examiner* — Tekchand Saidha
(74) *Attorney, Agent, or Firm* — Fay Sharpe LLP

(57) ABSTRACT

The present disclosure relates to a transformant for producing 2,5-furandicarboxylic acid. The transformant for producing 2,5-furandicarboxylic acid includes a *Pseudomonas putida* and at least one exogenous gene. The exogenous gene is an HmfH gene or an HMFO gene, and the exogenous gene is integrated into the chromosome of the *Pseudomonas putida*.

12 Claims, 19 Drawing Sheets
Specification includes a Sequence Listing.

TRANSFORMANT FOR PRODUCING 2,5-FURANDICARBOXYLIC ACID AND PREPARATION METHOD FOR 2,5-FURANDICARBOXYLIC ACID

RELATED APPLICATIONS

This application claims priority to Taiwan Application Serial Number 108147257, filed Dec. 23, 2019, which is herein incorporated by reference.

SEQUENCE LISTING

The sequence listing submitted via EFS, in compliance with 37 CFR § 1.52(e)(5), is incorporated herein by reference. The sequence listing text file submitted via EFS contains the file "CP-4600-US_SEQ_LIST", created on Sep. 21, 2020, which is 49,928 bytes in size.

BACKGROUND

Technical Field

The present disclosure relates to a transformant of *Pseudomonas putida*. More particularly, the present disclosure relates to a transformant for producing 2,5-furandicarboxylic acid and a preparation method for 2,5-furandicarboxylic acid.

Description of Related Art

Since 2004, the US Department of Energy has specifically pointed out that 2,5-furandicarboxylic acid is one of the most important high-value chemicals in the world that can be converted from biomass. 2,5-Furandicarboxylic acid is the precursor of polyethylene furanoate (PEF), which is an alternative raw material for the current plastic raw material produced from petroleum resources—polyethylene terephthalate (PET). PEF retains the characteristics of PET but also has biodegradability, which has a smaller impact on the environment and has more potential. In addition, 2,5-furandicarboxylic acid has broad application prospects, for example, it can synthesize polybutylene terephthalate (PBT) and polypropylene terephthalate (PPT), and can be used as a precursor material for succinic acid and bio-nylon. The aforementioned downstream products can produce billions of euros in the raw material market every year.

In recent years, many research results report that 5-hydroxymethylfurfural (HMF) can be converted into 2,5-furandicarboxylic acid by chemical or biological methods. 5-Hydroxymethylfurfural is an intermediate platform compound for multiple purposes. 5-Hydroxymethylfurfural can be obtained from the dehydration reaction of fructose or glucose, or can be obtained from hydrolysates lignocellulose, which is the renewable raw material that contains the most sugar on the earth. Therefore, the development of technology to produce various specialty chemicals or biomass fuels with lignocellulose as a material source is the trend of the times.

Although the production efficiency of 2,5-furandicarboxylic acid prepared by chemical method is relatively high, it usually requires high temperature, high pressure operating conditions and expensive catalysts such as platinum or gold, and it will produce waste liquid with high salt and organic compounds. In addition to the expensive manufacturing process, improper handling of waste liquid also affects the environment. The biological method of 5-hydroxymethyl furfural to produce 2,5-furandicarboxylic acid is relatively mild. The biological method only need to culture microorganisms in culture medium to perform the whole-cell biological conversion. It does not require high temperature and high pressure operation, does not produce organic salts and waste acids, and has relatively low toxicity to the environment. When using the biological method to produce 2,5-furandicarboxylic acid, *Pseudomonas putida* transformed with enzyme gene expression plasmids is used as a production plant. However, the aforementioned biological method is often unstable and requires additional antibiotics to maintain the enzyme performance, so that the condition is not conducive to mass production for industrial use.

SUMMARY

According to one aspect of the present disclosure, a transformant for producing 2,5-furandicarboxylic acid is provided. The transformant for producing 2,5-furandicarboxylic acid includes a host cell and at least one exogenous gene. The host cell is *Pseudomonas putida*. The at least one exogenous gene is a HmfH gene including a nucleic acid sequence of SEQ ID NO: 1 or a HMFO gene including a nucleic acid sequence of SEQ ID NO: 2, and the at least one exogenous gene is integrated in a chromosome of the host cell.

According to another aspect of the present disclosure, a preparation method for 2,5-furandicarboxylic acid includes steps as follows. A reaction substrate is provided, and the reaction substrate includes 5-hydroxymethylfurfural. A fermentation step is performed. In the fermentation step, reaction substrate is inoculated with the transformant for producing 2,5-furandicarboxylic acid according to the aforementioned aspect, and then is cultured at a fermentation temperature for a fermentation time to obtain a fermented substance. The fermented substance includes the 2,5-furandicarboxylic acid.

BRIEF DESCRIPTION OF THE DRAWINGS

The present disclosure can be more fully understood by reading the following detailed description of the embodiment, with reference made to the accompanying drawings as follows.

DETAILED DESCRIPTION

Transformant for Producing 2,5-Furandicarboxylic Acid

One object of the present disclosure is to provide a transformant that can efficiently convert 5-hydroxymethylfurfural (hereinafter referred to as "HMF") into 2,5-furandicarboxylic acid (hereinafter referred to as "FDCA"). In previously studies, enzymes including AAO, CPO, HMFO, UPO, PAMO, GOase, and HmfH can convert HMF to FDCA. Because the conversion of HMF to FDCA has several intermediate products, the conversions that can be catalyzed by various enzymes are not the same. In addition, the conversion of HMF to FDCA in previous studies is usually catalyzed in vitro and requires an additional protein extraction step, which is costly and time-consuming. Therefore, before preparing a transformant for producing 2,5-furandicarboxylic acid of the present disclosure, the ability of each enzyme to convert HMF into its derivatives is analyzed first to screen for enzymes suitable for catalyzing in vivo FDCA production in *Pseudomonas putida* as biocatalysts without any further purification.

Figure 1A:
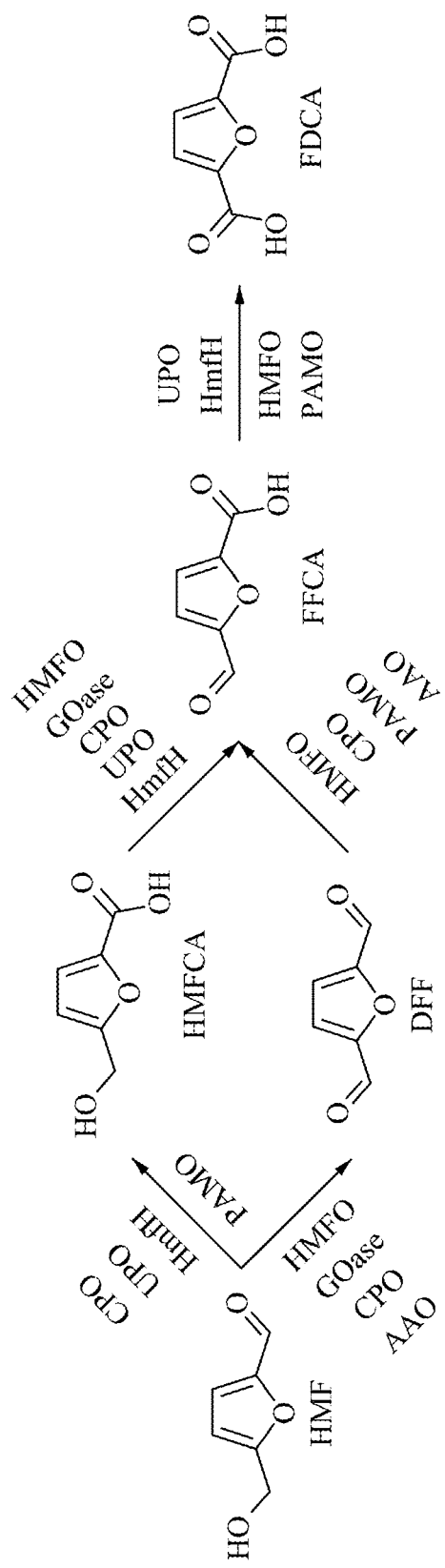
FIG. 1A is a schematic view showing reaction pathway of 5-hydroxymethylfurfural and reaction of each enzyme.

Please refer to FIG. 1A, which is a schematic view showing reaction pathway of HMF and reaction of each enzyme. In FIG. 1A, the pathway of converting HMF to FDCA can be that HMF is converted to 5-hydroxymethyl-2-furancarboxylic acid (hereinafter referred to as "HMFCA"), followed by conversion to 5-formyl-2-furancarboxylic acid (hereinafter referred to as "FFCA") and then FDCA. HMF can also be converted to 2,5-diformylfuran (hereinafter referred to as "DFF"), followed by conversion to FFCA and then FDCA. HmfH, HMFO, AAO, CPO, UPO, PAMO and GOase participate in different pathways.

Figure 1B:
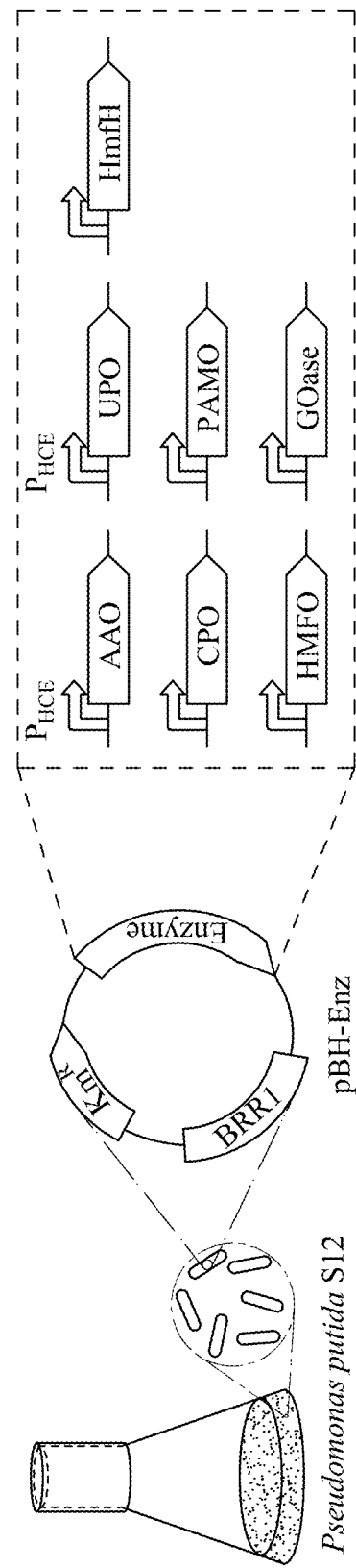
FIG. 1B is a schematic view showing constructions of plasmids of different enzymes.

Please refer to FIG. 1B, which is a schematic view showing constructions of plasmids of different enzymes. A set of enzyme-expressing plasmids are constructed, in which the enzyme gene is constructed downstream of the strong constitutive HCE promoter ($P_{HCE}$) of the template plasmid pBBR1, and the antibiotic resistance gene of the template plasmid pBBR1 is replaced with kanamycin resistance gene ($Km^R$). The constructed enzyme-expressing plasmids are respectively electroporated into *Pseudomonas putida* S12, and then cultured in a reaction substrate including HMF to observe the ability of each enzyme to convert HMF into downstream derivatives. The tested enzymes include HmfH, HMFO, AAO, CPO, UPO, PAMO, and GOase. The nucleotide sequence of HmfH gene encoding HmfH is referenced as SEQ ID NO: 1, the nucleotide sequence of the HMFO gene encoding HMFO is referenced as SEQ ID NO: 2, the nucleotide sequence of the AAO gene encoding AAO is referenced as SEQ ID NO: 3, the nucleotide sequence of the CPO gene encoding CPO is referenced as SEQ ID NO: 4, the nucleotide sequence of the UPO gene encoding UPO is referenced as SEQ ID NO: 5, the nucleotide sequence of the PAMO gene encoding PAMO is referenced as SEQ ID NO: 6, and the nucleotide sequence of the GOase gene encoding GOase is referenced as SEQ ID NO: 7.

Figure 1C:
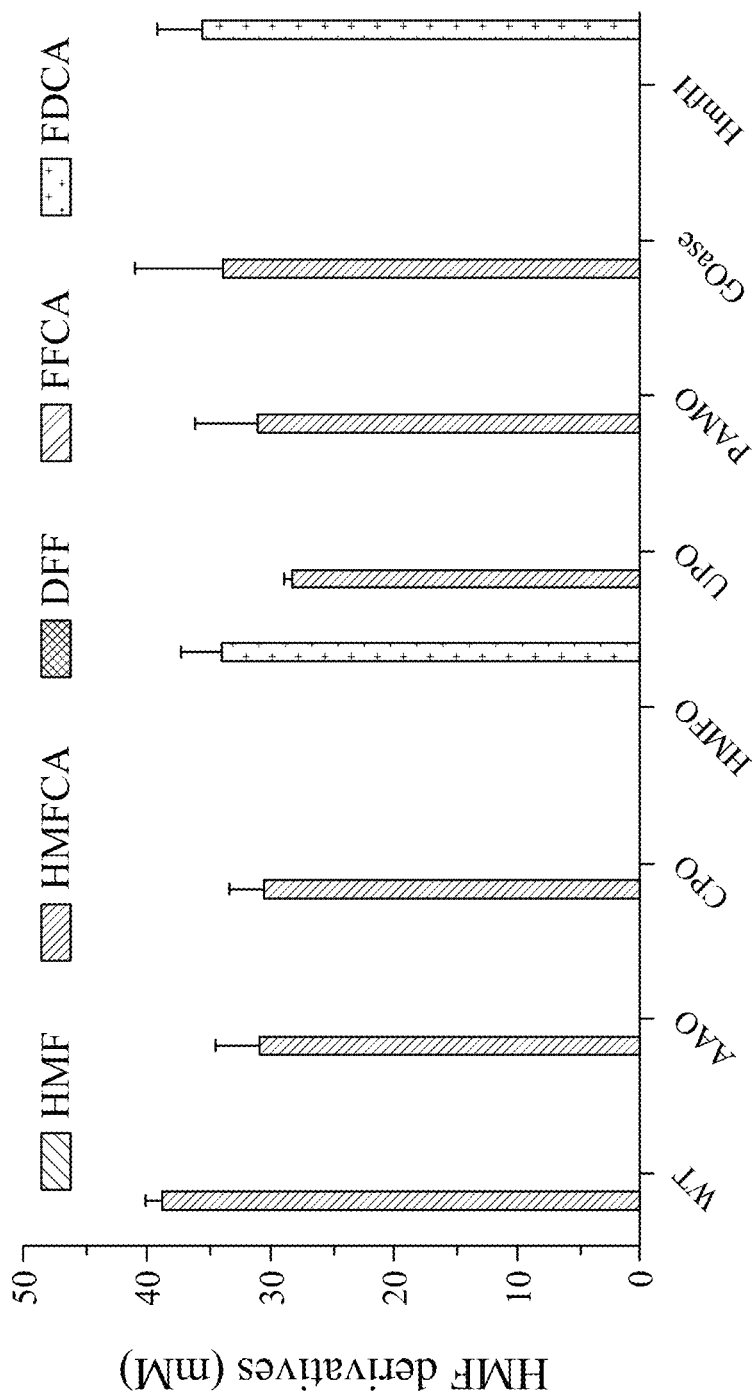
FIG. 1C shows analytical results of the conversion of 5-hydroxymethylfurfural to its derivatives by enzymes.

Please refer to FIG. 1C, which shows analytical results of the conversion of HMF to its derivatives by enzymes, wherein WT represents the wildtype *Pseudomonas putida* S12, and AAO, CPO, HMFO, UPO, PAMO, GOase and HmfH represent the transformant with AAO gene, CPO gene, HMFO gene, UPO gene, PAMO gene, GOase gene and HmfH gene, respectively. In FIG. 1C, all groups including the wildtype *Pseudomonas putida* S12 can 100% convert HMF to downstream derivatives, which indicate that the endogenous enzyme ALDH of the *Pseudomonas putida* S12 can effectively convert HMF to HMFCA. However, only the group expressing HMFO gene and HmfH gene can directly convert HMF to FDCA. Therefore, the HMFO gene including a nucleic acid sequence of SEQ ID NO: 1 and/or the HMFO gene including a nucleic acid sequence of SEQ ID NO: 2 are selected as the at least one exogenous gene that are subsequently integrated in the chromosome of the *Pseudomonas putida*.

A transformant for producing 2,5-furandicarboxylic acid of the present disclosure includes a host cell and at least one exogenous gene. The host cell is the *Pseudomonas putida*. The at least one exogenous gene is the HmfH gene including the nucleic acid sequence of SEQ ID NO: 1 or the HMFO gene including the nucleic acid sequence of SEQ ID NO: 2, and the at least one exogenous gene is integrated in a chromosome of the host cell.

Figure 2A:
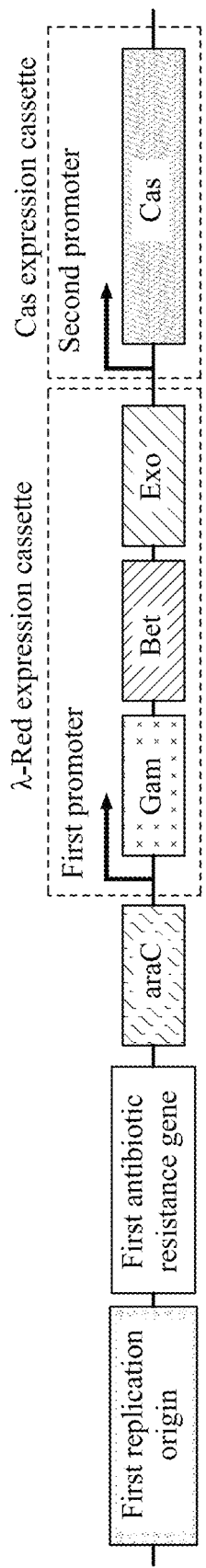
FIG. 2A is a schematic view showing a construction of a RedCas expression plasmid.
Figure 2B:
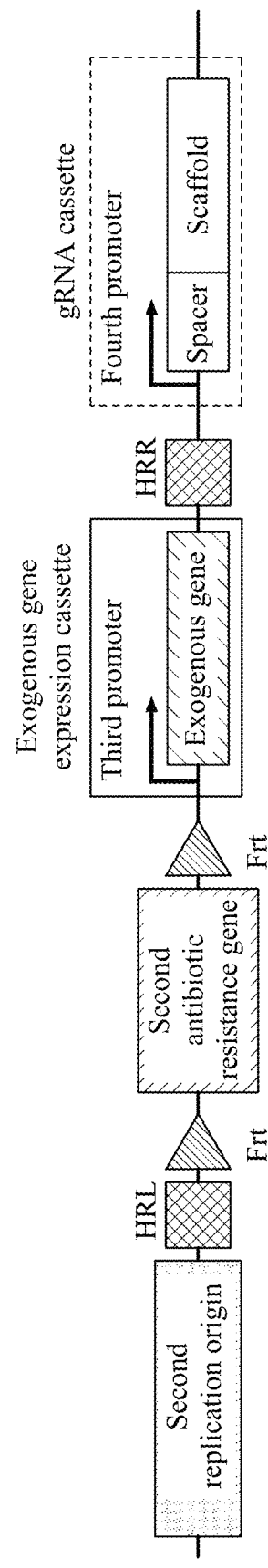
FIG. 2B is a schematic view showing a construction of an exogenous gene expression plasmid.

In one example of the present disclosure, the at least one exogenous gene of the transformant for producing 2,5-furandicarboxylic acid is integrated in a chromosome of a host cell using a gene editing system. The gene editing system includes a RedCas expression plasmid and an exogenous gene expression plasmid. Please refer to FIGS. 2A and 2B. FIG. 2A is a schematic view showing a construction of a RedCas expression plasmid, and FIG. 2B is a schematic view showing a construction of an exogenous gene expression plasmid.

The RedCas expression plasmid successively includes a first replication origin, a first antibiotic resistance gene, a λ-Red expression cassette and a Cas expression cassette, in which the first replication origin includes a nucleic acid sequence of SEQ ID NO: 8, the λ-Red expression cassette includes a first promoter, a Gam gene, a Bet gene and an Exo gene, and the Cas expression cassette includes a second promoter and a Cas gene. Preferably, the Cas gene can include a nucleic acid sequence of SEQ ID NO: 16, a nucleic acid sequence of SEQ ID NO: 17 or a nucleic acid sequence of SEQ ID NO: 18, and the RedCas expression plasmid can further include an araC gene.

The exogenous gene expression plasmid successively includes a second replication origin, a left homology arm, a second antibiotic resistance gene, an exogenous gene expression cassette, a right homology arm and a gRNA cassette. The exogenous gene expression cassette includes a third promoter and at least one exogenous gene, and the at least one exogenous gene is a HmfH gene including a nucleic acid sequence of SEQ ID NO: 1 or a HMFO gene including a nucleic acid sequence of SEQ ID NO: 2. The gRNA cassette includes a fourth promoter and a gRNA sequence, and the gRNA sequence is composed of a spacer and a scaffold. The left homology arm and the right homology arm compose a homology region. A sequence of the homology region is homologous to a first specific sequence of a chromosome of the *Pseudomonas putida*, and a sequence of the spacer is homologous to a second specific sequence of the chromosome of the *Pseudomonas putida*. The first antibiotic resistance gene and the second antibiotic resistance gene are different. Preferably, the exogenous gene expression plasmid can further include two Flp/FRT knockout sequences, and the second antibiotic resistance gene is located between the two Flp/FRT knockout sequences.

In one example of the present disclosure, a number of the at least one exogenous gene of the transformant for producing 2,5-furandicarboxylic acid can be two, and the two exogenous gene are the same or different. For example, the two exogenous genes can be one HmfH gene and one HMFO gene, two HmfH genes or two HMFO genes. Preferably, when the at least one exogenous gene is the HmfH gene, the at least one exogenous gene can further include a HmfT1 gene. The *Pseudomonas putida* can be the *Pseudomonas putida* S12.

Examples 1-3

In order to prepare the transformant for producing 2,5-furandicarboxylic acid that can stably express the exogenous gene, three different CRISPR/Cas systems including SpCas9, SaCas9 and FnCas12a are constructed in the experiment, and gRNA corresponds to the Upp site of the chromosome of the *Pseudomonas putida* (PP_0746) is designed, respectively. The *Pseudomonas putida* used in the experiment is the *Pseudomonas putida* S12.

Figure 3A:
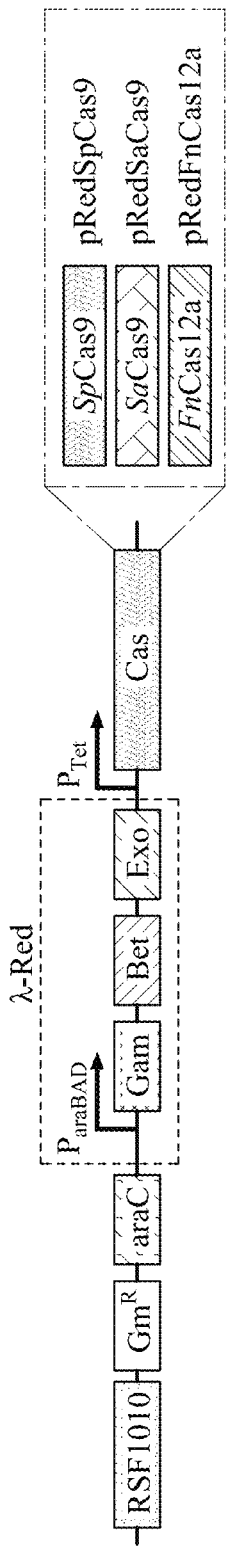
FIG. 3A is a schematic view showing constructions of the RedCas expression plasmid used in transformants of Example 1, Example 2 and Example 3 of according to one embodiment of the present disclosure.

Please refer to FIG. 3A, which is a schematic view showing constructions of the RedCas expression plasmid used in transformants of Example 1, Example 2 and Example 3 of according to one embodiment of the present disclosure. The RedCas expression plasmid used in transformants of Examples 1 to 3 successively includes a first replication origin, a first antibiotic resistance gene, a araC gene, a λ-Red expression cassette and a Cas expression cassette, in which the first replication origin is RSF1010 ori with the nucleotide sequence referenced as SEQ ID NO: 8, the first antibiotic resistance gene is gentamicin resistance ($Gm^R$) gene with the nucleotide sequence referenced as SEQ ID NO: 9, the nucleotide sequence of the araC gene is referenced as SEQ ID NO: 10. The λ-Red expression cassette includes a first promoter, a Gam gene, a Bet gene and an Exo gene, in which the first promoter is araBAD promoter with the nucleotide sequence referenced as SEQ ID NO: 11, the nucleotide sequence of the Gam gene is referenced as SEQ ID NO: 12, the nucleotide sequence of the Bet gene is referenced as SEQ ID NO: 13, and the nucleotide sequence of the Exo gene is referenced as SEQ ID NO: 14. The Cas expression cassette includes a second promoter and a Cas gene, in which the second promoter is Tet promoter with the nucleotide sequence referenced as SEQ ID NO: 15. The RedCas expression plasmids used in the transformants of Example 1, Example 2 and Example 3 are pRedSpCas9 plasmid, pRedSaCas9 plasmid and pRedFnCas12a plasmid, respectively. The nucleotide sequence of the Cas gene of the pRedSpCas9 plasmid is referenced as SEQ ID NO: 16, the nucleotide sequence of the Cas gene of the pRedSaCas9 plasmid is referenced as SEQ ID NO: 17, and the nucleotide sequence of the Cas gene of the pRedFnCas12a plasmid is referenced as SEQ ID NO: 18.

Figure 3B:
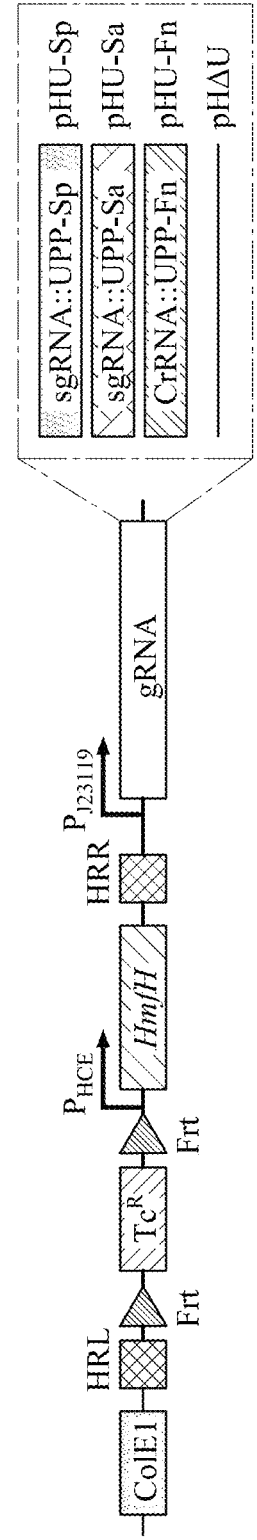
FIG. 3B is a schematic view showing a construction of the exogenous gene expression plasmid used in the transformants of Example 1, Example 2 and Example 3 according to one embodiment of the present disclosure.

Please refer to FIG. 3B, which is a schematic view showing a construction of the exogenous gene expression plasmid used in the transformants of Example 1, Example 2 and Example 3 according to one embodiment of the present disclosure. The exogenous gene expression plasmid used in transformants of Examples 1 to 3 successively includes a second replication origin, a left homology arm, a Flp/FRT knockout sequence, a second antibiotic resistance gene, an exogenous gene expression cassette, a right homology arm and a gRNA cassette. The second replication origin is ColE1 ori with the nucleotide sequence referenced as SEQ ID NO: 19, the nucleotide sequence of the left homology arm is referenced as SEQ ID NO: 20, the nucleotide sequence of the Flp/FRT knockout sequence is referenced as SEQ ID NO: 21, and the second antibiotic resistance gene is tetracycline resistance ($Tc^R$) gene with the nucleotide sequence referenced as SEQ ID NO: 22. The exogenous gene expression cassette includes a third promoter and at least one exogenous gene. The third promoter is HCE promoter with the nucleotide sequence referenced as SEQ ID NO: 23, and the exogenous gene is HmfH gene with the nucleotide sequence referenced as SEQ ID NO: 1 as an example. The nucleotide sequence of the right homology arm is referenced as SEQ ID NO: 24. The gRNA cassette includes a fourth promoter and a gRNA sequence, and the gRNA sequence is composed of a spacer and a scaffold. The fourth promoter is J23119 promoter with the nucleotide sequence referenced as SEQ ID NO: 25. The exogenous gene expression plasmids used in the transformants of Example 1, Example 2 and Example 3 of the present disclosure are pHU-Sp plasmid, pHU-Sa plasmid and pHU-Fn plasmid, respectively. The nucleotide sequence of the gRNA sequence of the pHU-Sp plasmid is referenced as SEQ ID NO: 26, the nucleotide sequence of the gRNA sequence of the pHU-Sa plasmid is referenced as SEQ ID NO: 27, and the nucleotide sequence of the gRNA sequence of the pHU-Fn plasmid is referenced as SEQ ID NO: 28. In addition, pHΔU plasmid is constructed as a control group, which does not trigger double strand break on the chromosome of the *Pseudomonas putida*. The left homology arm and the right homology arm compose the homology region. The sequence of the homology region is homologous to the first specific sequence of the chromosome of the *Pseudomonas putida*, the sequence of the spacer is homologous to Upp site of the chromosome of the *Pseudomonas putida*, and the scaffold interacts with the Cas protein.

Figure 3C:
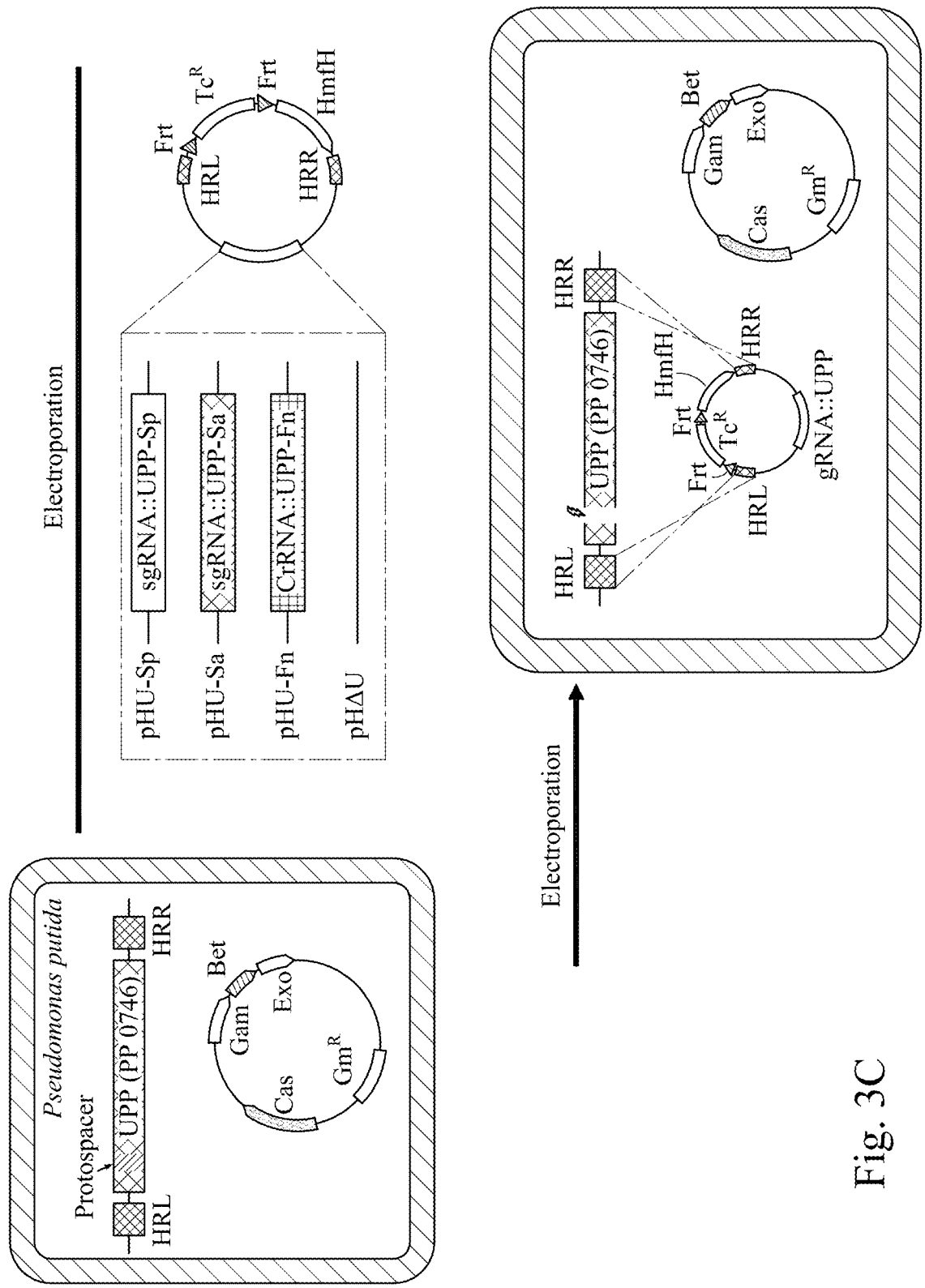
FIG. 3C is a schematic view showing operation of integrating an exogenous gene into a chromosome of the *Pseudomonas putida*.

Please refer to FIG. 3C, which is a schematic view showing operation of integrating the exogenous gene into the chromosome of the *Pseudomonas putida*. The constructed RedCas expression plasmid (pRedSpCas9 plasmid, pRedSaCas9 plasmid, and pRedFnCas12a plasmid) is transformed into the *Pseudomonas putida* by electroporation to obtain the transformant, respectively. Further, the transformant can be cultured using LB medium containing gentamicin to select the transformant that successfully transformed the RedCas expression plasmid. The transformant is cultured in 30 mL of fresh LB medium containing gentamicin overnight, and then cultured with 0.5% arabinose for another 2 hours to induce the RedCas expression plasmid expresses the Gam protein, the Beta protein, the Exo protein and the Cas protein. The inducted transformant is collected by centrifugation and washed twice with 300 mM sucrose. Then, the exogenous gene expression plasmid (pHU-Sp plasmid, pHU-Sa plasmid and pHU-Fn plasmid) is transformed into the corresponding transformant by electroporation to obtain the transformants of Example 1, Example 2 and Example 3, respectively. Further, the transformants of Example 1, Example 2 and Example 3 can be cultured in SOC medium without antibiotic for 4 hours to recover and then be spread onto tetracycline-containing LB-agar plate. The transformants of Example 1, Example 2 and Example 3 are cultured, so that the exogenous gene expression plasmids express the gRNA. The gRNA and the Cas protein form a Cas protein complex triggering the double strand break on the second specific sequence of the chromosome of the second transformant, and the Gam protein, the Beta protein and the Exo protein co-guide the homology region of the exogenous gene expression plasmid to perform homologous recombination with the first specific sequence of the chromosome of the transformants of Example 1, Example 2 and Example 3, so that the HmfH gene is inserted into the Upp site of the chromosome of the transformants of Example 1, Example 2 and Example 3 to obtain the homologous recombinants.

To confirm that the exogenous gene is indeed integrated in the chromosome of the transformants of Example 1, Example 2 and Example 3, after transforming the constructed plasmid into the *Pseudomonas putida*, the obtained transformants of Example 1, Example 2 and Example 3 are selected by culturing in the medium containing tetracycline. The number of survival colonies represents the number of the transformants of Example 1, Example 2 and Example 3 that homologously recombine the exogenous gene into the chromosomes.

Figure 4A:
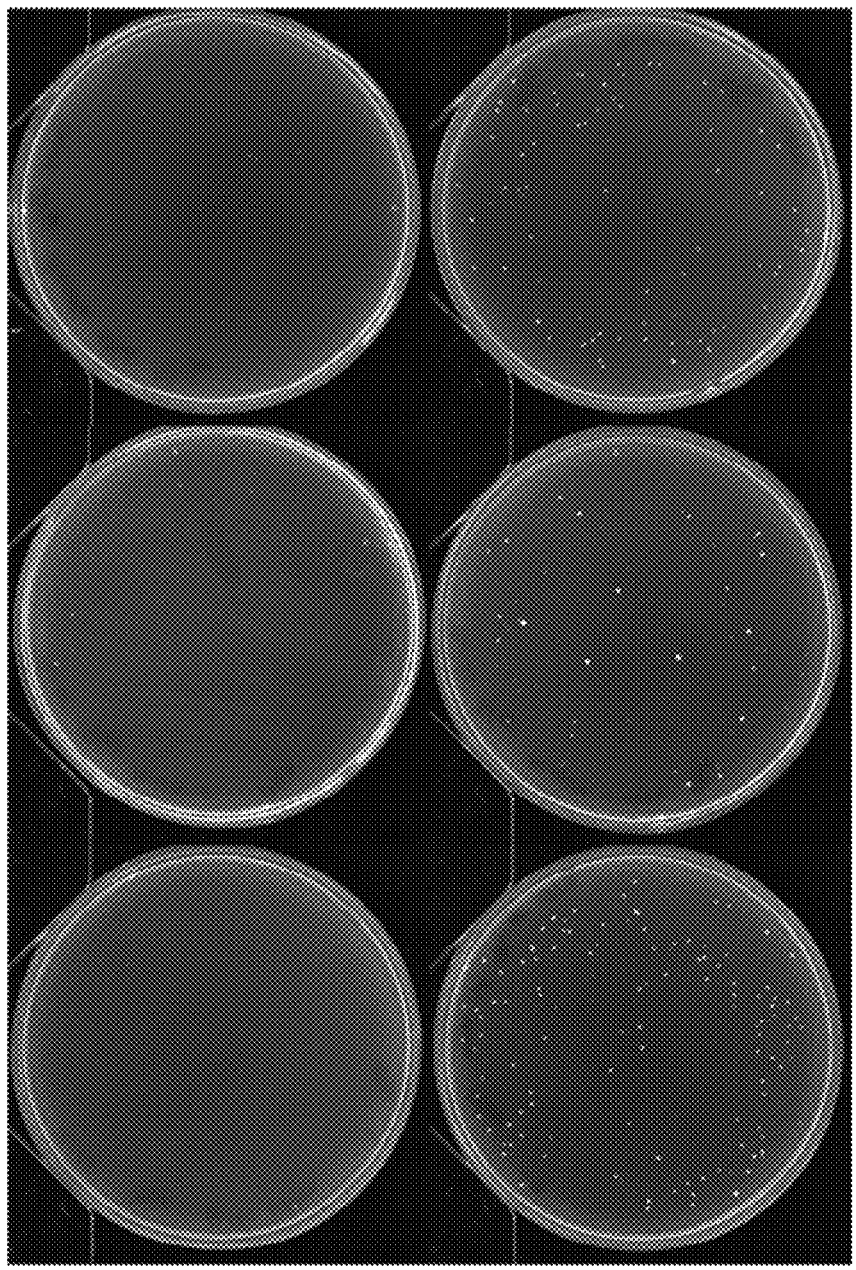
FIG. 4A is a qualitative diagram of survival colonies of the transformants of Example 1, Example 2 and Example 3 of the present disclosure.
Figure 4C:
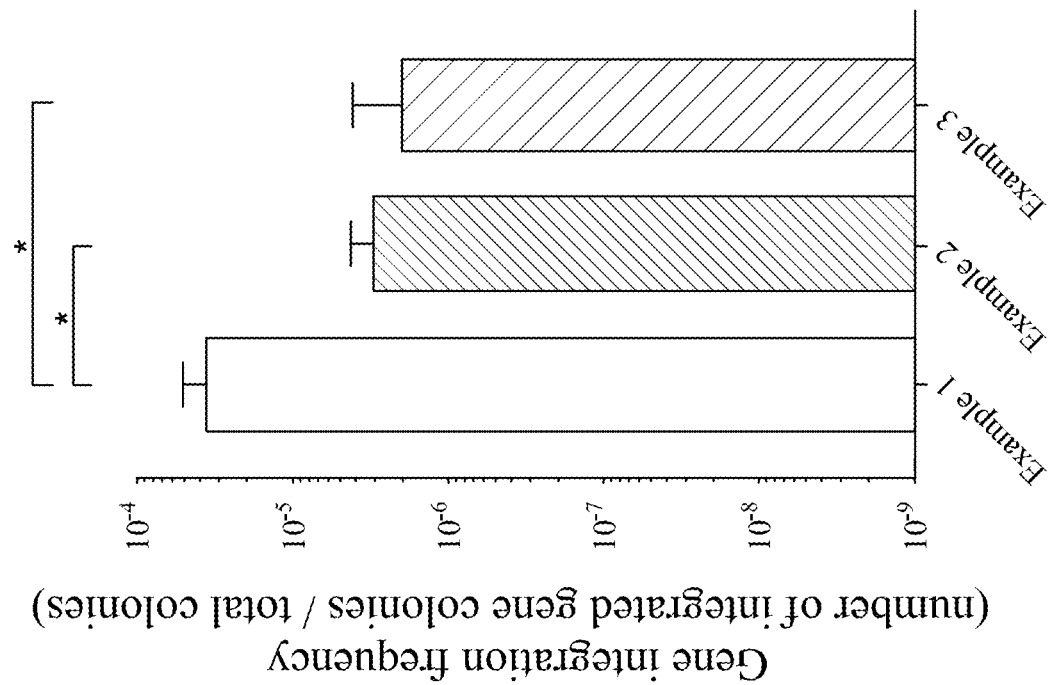
FIG. 4C is a quantitative diagram of survival colonies of the transformants of Example 1, Example 2 and Example 3 of the present disclosure.
Figure 4B:
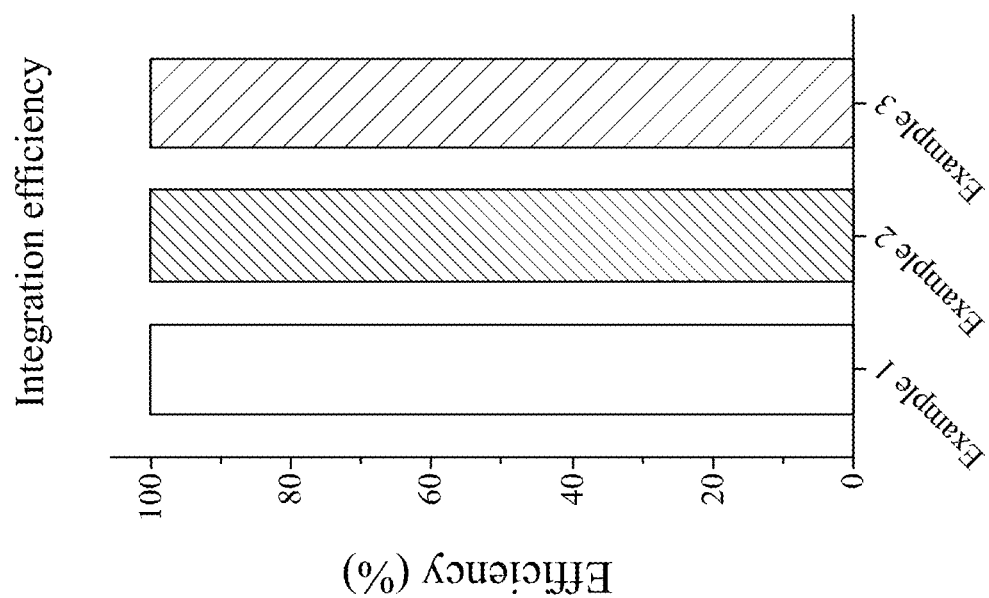
FIG. 4B shows analytical results of the homologous recombination efficiency of the transformants of Example 1, Example 2 and Example 3 of the present disclosure.

Please refer to FIGS. 4A, 4B and 4C. FIG. 4A is a qualitative diagram of survival colonies of the transformants of Example 1, Example 2 and Example 3 of the present disclosure. FIG. 4B shows analytical results of the homologous recombination efficiency of the transformants of Example 1, Example 2 and Example 3 of the present disclosure. FIG. 4C is a quantitative diagram of survival colonies of the transformants of Example 1, Example 2 and Example 3 of the present disclosure.

In FIG. 4A, survival colonies can be obviously observed in the transformants of Example 1, Example 2 and Example 3 with gRNA (pHU), but no survival colony can be observed in the control groups without gRNA (pHΔU). The results indicate that the λ-Red system alone cannot effectively integrate the exogenous gene into the chromosome of the *Pseudomonas putida* without the double strand break triggered by the CRISPR system, so that the integration efficiency of the exogenous gene is very low. In addition, the survival rates of the transformants of Example 1, Example 2 and Example 3 are calculated by taking the total number of the survival colonies without antibiotic as the denominator, and the number of the survival colonies with antibiotic (that is the number of the colonies successfully integrate the exogenous gene) as the numerator. In FIGS. 4B and 4C, the integration efficiency of the exogenous gene in the transformants of Example 1, Example 2 and Example 3 can reach nearly 100%, and the survival rate of the transformant of Example 1 is higher than that of the transformants of Example 2 and Example 3.

Figure 5A:
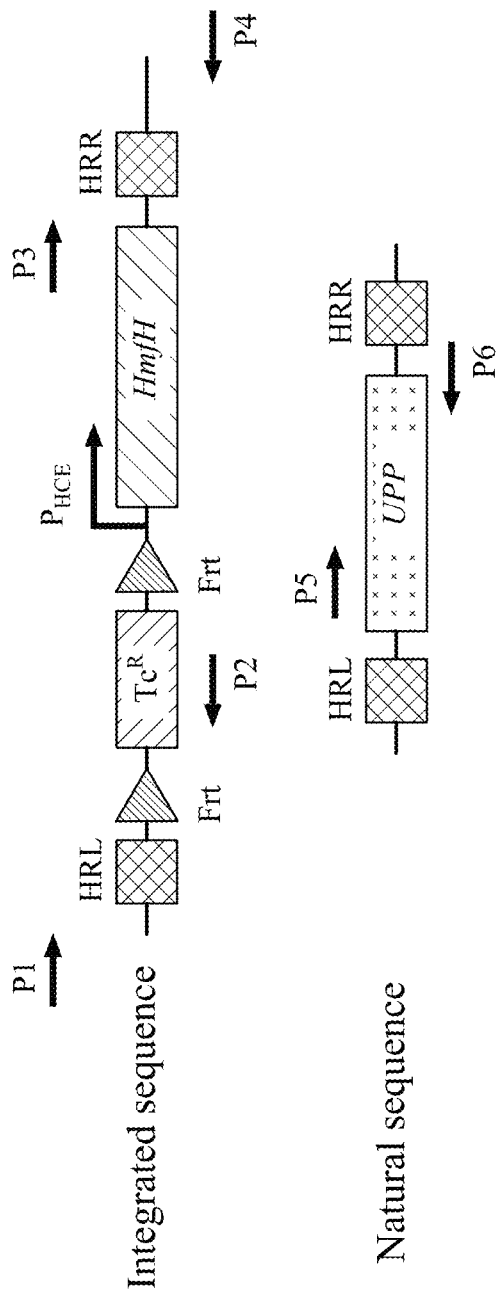
FIG. 5A is a schematic diagram showing the sites of 6 pairs of primers designed for the colony PCR.

Further, a colony PCR is used to confirm whether the exogenous gene is integrated into a precise site in the chromosome of the transformant for producing 2,5-furandicarboxylic acid of the present disclosure. Please refer to FIG. 5A, which is a schematic diagram showing the sites of 6 pairs of primers designed for the colony PCR. The primers of the colony PCR are designed at the junction of the chromosomes of the *Pseudomonas putida* and the ends of the exogenous gene. A size of left amplicon (P1+P2) is about 1.7 kb and the size of right amplicon (P3+P4) is about 1.5 kb. An amplicon of about 6.5 kb can be obtained by performing the colony PCR with primers P1 and P4 PCR. In addition, the primers P5 and P6 are designed according to the original sequence on the chromosome of the *Pseudomonas putida*. An amplicon of about 0.5 kb can be obtained by performing the colony PCR with primers P5 and P6, which means that the exogenous gene has not been successfully integrated into the chromosome of the *Pseudomonas putida*. The nucleotide sequence of the primer P1 is referenced as SEQ ID NO: 29, the nucleotide sequence of the primer P2 is referenced as SEQ ID NO: 30, the nucleotide sequence of the primer P3 is referenced as SEQ ID NO: 31, the nucleotide sequence of the primer P4 is referenced as SEQ ID NO: 32, the nucleotide sequence of the primer P5 is referenced as SEQ ID NO: 33, and the nucleotide sequence of the primer P6 is referenced as SEQ ID NO: 34.

Figure 5B:
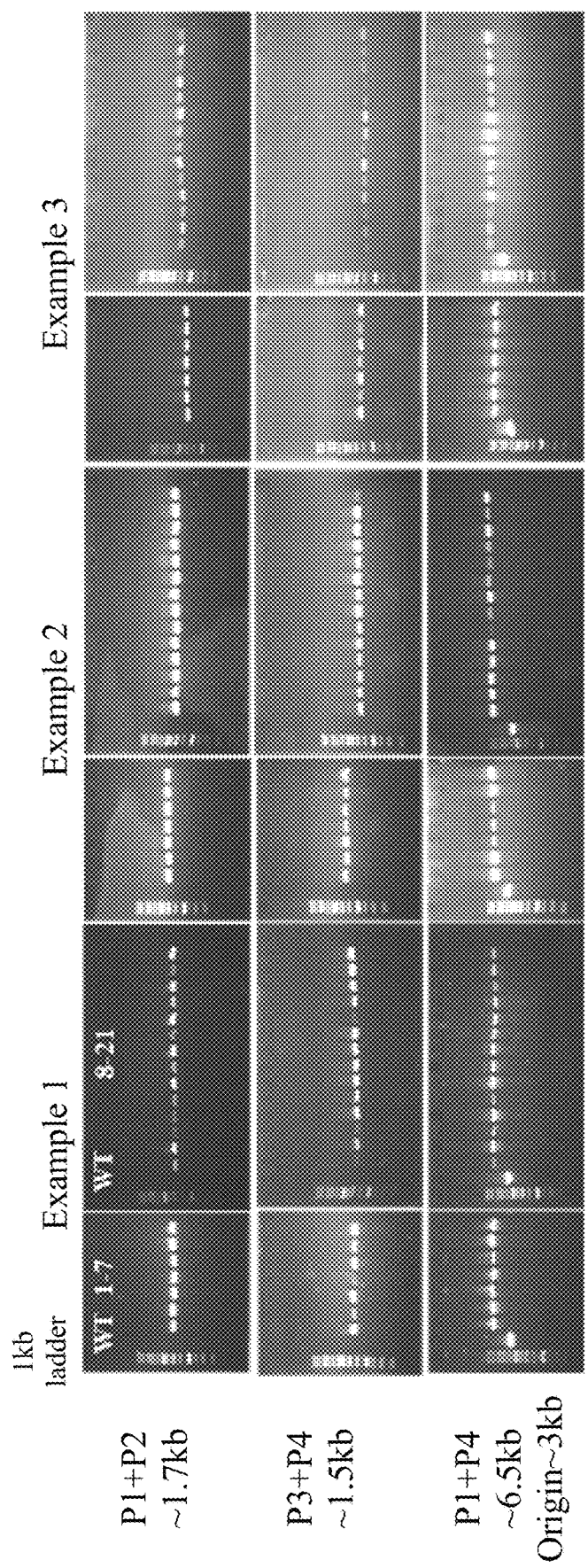
FIG. 5B shows analytical results of the colony PCR for confirming the integration of the exogenous gene in chromosomes of the transformants of Example 1, Example 2 and Example 3.

Please refer to FIG. 5B, which shows analytical results of the colony PCR for confirming the integration of the exogenous gene in chromosomes of the transformants of Example 1, Example 2 and Example 3. In FIG. 5B, 21 colonies are selected in the transformants of Example 1, Example 2 and Example 3, respectively, and the colony PCR is performed with primers P1 and P2 or P3 and P4. The results show that although the *Pseudomonas putida* has polyploid chromosomes, the exogenous gene of each of the selected colonies in the transformants of Example 1, Example 2 and Example 3 is successfully integrated in the target site. Thus, the exogenous gene is indeed integrated in each of the polyploid chromosomes of the transformants of Example 1, Example 2 and Example 3.

Figure 5C:
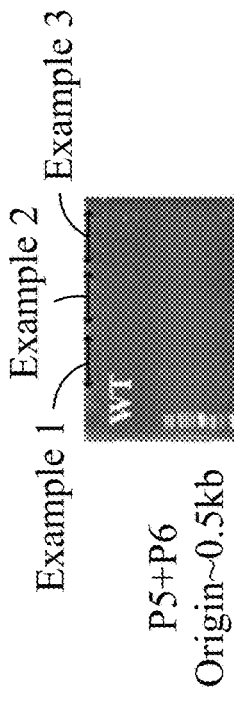
FIG. 5C shows analytical result of the colony PCR for confirming the existence of the original chromosome sequence of the transformants of Example 1, Example 2 and Example 3.

Please refer to FIG. 5C, which shows analytical result of the colony PCR for confirming the existence of the original chromosome sequence of the transformants of Example 1, Example 2 and Example 3. In FIG. 5C, 2 colonies are selected in the transformants of Example 1, Example 2 and Example 3, respectively, and the colony PCR is performed with primers P5 and P6. If the amplicon of about 0.5 kb is detected, it means that the Upp site of the *Pseudomonas putida* that should have been replaced still exists. It also means that the exogenous gene is integrated in the wrong site or the exogenous gene is not completely integrated in all polyploid chromosomes of the *Pseudomonas putida*. In FIG. 5C, no amplicon is detected in each of the selected colonies in the transformants of Example 1, Example 2 and Example 3. The results indicate that the exogenous gene is indeed integrated in the chromosomes of the transformants of Example 1, Example 2 and Example 3.

To confirm the stability of the exogenous gene of the transformant for producing 2,5-furandicarboxylic acid of the present disclosure, the transformant of Example 1 with the exogenous gene integrated in the correct site is cultured in LB medium without antibiotics for another 6 days (after 144 generations), and the colony PCR is used to further verify whether the integrated exogenous gene still exists at the target site on the chromosome of the transformant of Example 1. In addition, quantitative analysis of the expression of the exogenous gene is performed by quantitative PCR.

Figure 5E:
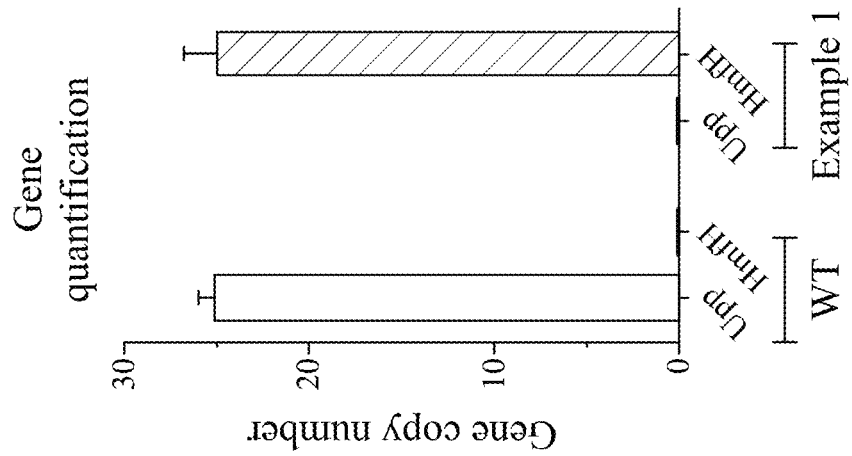
FIG. 5E is an analytical result showing gene copy number of the chromosome of the transformant of Example 1 which is integrated the exogenous gene.
Figure 5D:
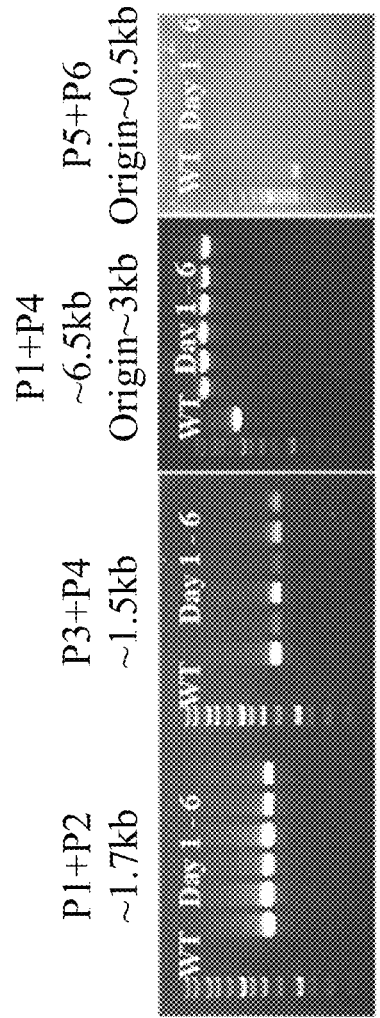
FIG. 5D shows analytical results of the colony PCR for confirming integration of the exogenous gene in the chromosome of the transformant of Example 1 after 6 days of transformation.

Please refer to FIGS. 5D and 5E. FIG. 5D shows analytical results of the colony PCR for confirming integration of the exogenous gene in the chromosome of the transformant of Example 1 after 6 days of transformation. FIG. 5E is an analytical result showing gene copy number of the chromosome of the transformant of Example 1 which is integrated the exogenous gene.

In FIG. 5D, the exogenous gene is still present at the target site of the chromosome of each of the selected colonies in the transformant of Example 1 after 144 generations of cultivation. In FIG. 5E, after 144 generations of cultivation, the transformant of Example 1 can stably express the exogenous gene (HmfH gene) in the 25 copies of chromosomes in the *Pseudomonas putida* S12, and does not express the Upp gene of the original sequence of the *Pseudomonas putida*. The results indicate that the transformant for producing 2,5-furandicarboxylic acid of the present disclosure can perform long-term stable expression of the integrated exogenous gene in the polyploid chromosomes.

Preparation Method for 2,5-Furandicarboxylic Acid

Figure 6:
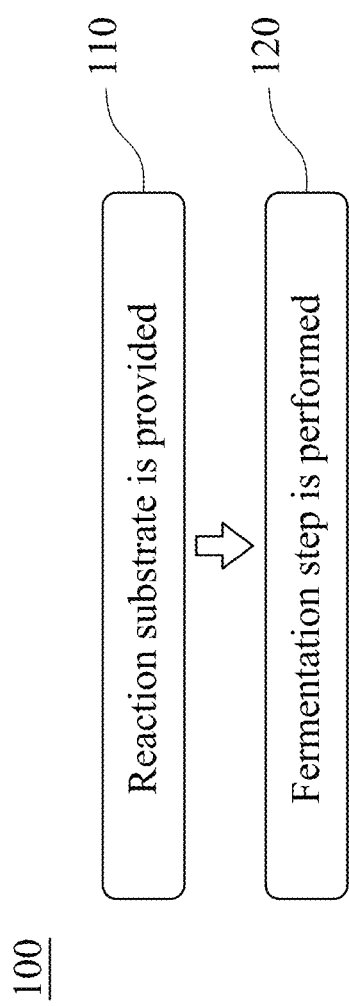
FIG. 6 is a flow diagram showing a preparation method for 2,5-furandicarboxylic acid according to another embodiment of the present disclosure.

Please refer to FIG. 6, which is a flow diagram showing a preparation method for 2,5-furandicarboxylic acid according to another embodiment of the present disclosure. In FIG. 6, the preparation method for 2,5-furandicarboxylic acid 100 includes a Step 110 and a Step 120.

In the Step 110, a reaction substrate is provided. The reaction substrate includes HMF. Preferably, an initial concentration of HMF in the reaction substrate can be 50 mM to 250 mM. In addition, the reaction substrate can further include manganese dioxide and/or calcium carbonate. The addition amount of manganese dioxide in the reaction substrate can be 0.1 g/L to 1 g/L, and the addition amount of calcium carbonate in the reaction substrate can be 5 g/L to 60 g/L. Preferably, the addition amount of manganese dioxide in the reaction substrate can be 0.5 g/L, and the addition amount of calcium carbonate in the reaction substrate can be 30 g/L.

In the Step 120, a fermentation step is performed. In the fermentation step, reaction substrate is inoculated with the transformant for producing 2,5-furandicarboxylic acid of the present disclosure, and then is cultured at a fermentation temperature for a fermentation time to obtain a fermented substance. The fermented substance includes the FDCA. Preferably, the fermentation temperature can be 30° C., and the fermentation time can be 24 hours.

Reference will now be made in detail to the present embodiments of the present disclosure, examples of which are illustrated in the accompanying drawings.

1.1 Example 1 and Example 4

To confirm that the preparation method for 2,5-furandicarboxylic acid of the present disclosure can efficiently convert HMF in the reaction substrate into FDCA, the transformant for producing 2,5-furandicarboxylic acid with the HmfH gene or the HMFO gene is prepared, respectively. Further, the transformants for producing 2,5-furandicarboxylic acid of the present disclosure are used to produce FDCA by the preparation method for 2,5-furandicarboxylic acid of the present disclosure.

Firstly, the constructed pRedSpCas9 plasmid is transformed into the *Pseudomonas putida* by electroporation, and cultured in LB medium including gentamicin to select the transformant that successfully transformed the RedCas expression plasmid. Then the exogenous gene expression plasmid with the HmfH gene including the nucleic acid sequence of SEQ ID NO: 1 or the HMFO gene including the nucleic acid sequence of SEQ ID NO: 2 is respectively transformed into the transformant by electroporation to obtain the transformant of Example 1 (with the HmfH gene) and the transformant of Example 4 (with the HMFO gene). The mechanism of the insertion of the HmfH gene and the HMFO gene into the transformants of Example 1 and Example 4 is as described above, and will not be repeated here.

The transformants of Example 1 and Example 4 are respectively inoculated into the reaction substrate including 50 mM HMF, and fermented at 30° C. Samples are taken at 0, 1, 2, 3, 4, 5, 6, 12, and 24 hours of fermentation, and the content of HMF and other subsequent derivatives in the fermented substance are analyzed by HPLC (Shimadzu LC-20A), in which the column used is Thermo Scientific™ Hypersil™ BDS C18 column, and the photodiode array detector is set at wavelengths of, 250 nm (HMFCA), 254 nm (FDCA) and 285 nm (HMF, DFF, and FFA).

Figure 7A:
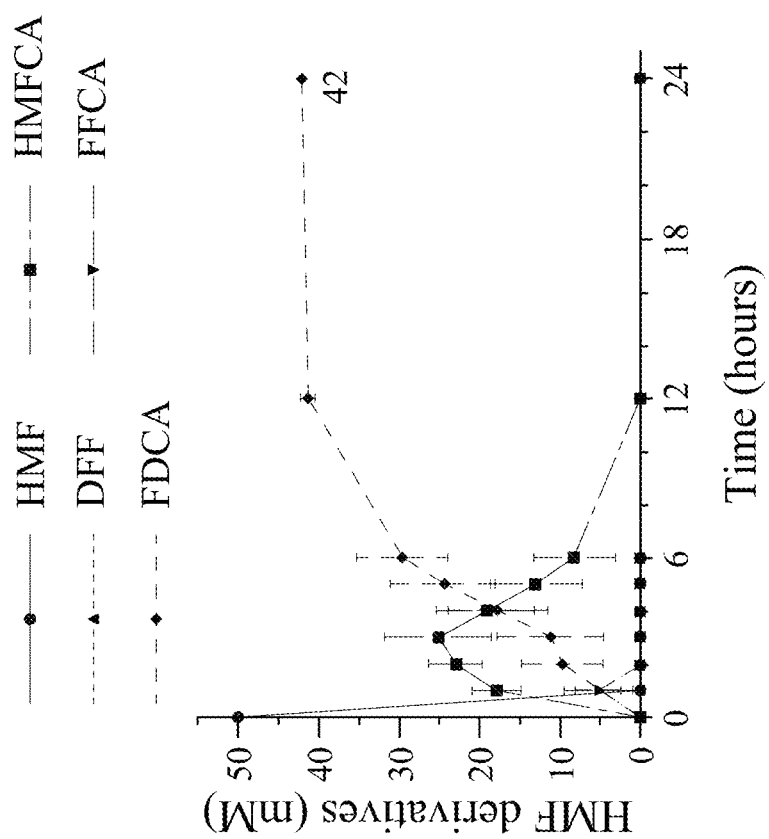
FIG. 7A shows an analytical result of the efficiency of the transformant of Example 1 in converting 5-hydroxymethylfurfural to 2,5-furandicarboxylic acid.
Figure 7B:
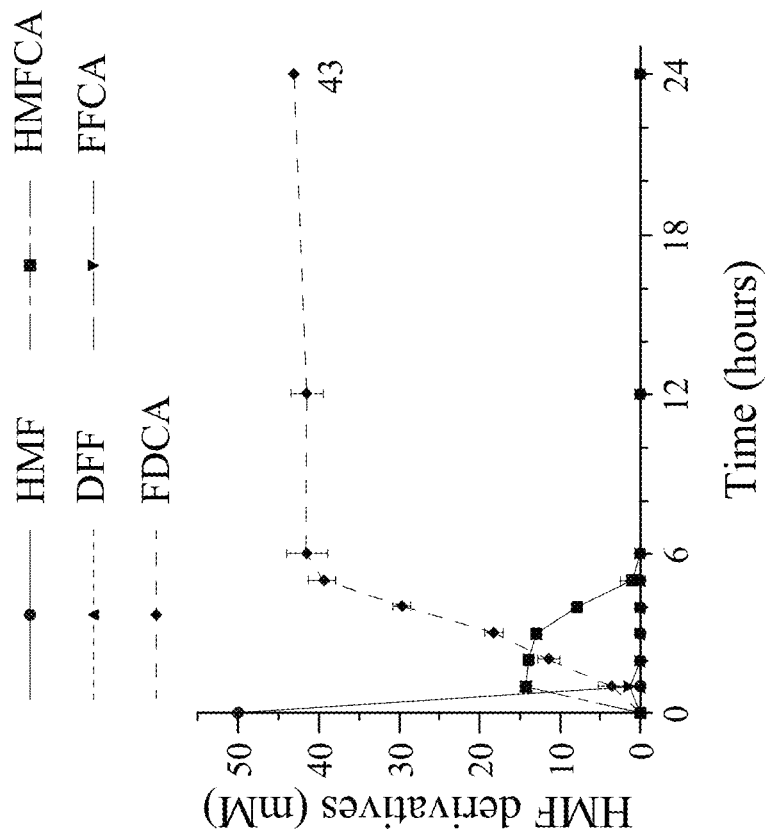
FIG. 7B shows an analytical result of the efficiency of the transformant of Example 4 in converting 5-hydroxymethylfurfural to 2,5-furandicarboxylic acid.

Please refer to FIGS. 7A and 7B. FIG. 7A shows an analytical result of the efficiency of the transformant of Example 1 in converting HMF to FDCA, and FIG. 7B shows an analytical result of the efficiency of the transformant of Example 4 in converting HMF to FDCA. When the initial concentration of HMF is 50 mM, the final concentrations of FDCA converted from HMF by the transformant of Example 1 and the transformant of Example 4 are similar. However, the concentration of FDCA is 43 mM within 6 hours in the group inoculated with the transformant of Example 1, while the group inoculated with the transformant of Example 4 requires more than 6 hours to complete the conversion of FDCA. The above results indicate that the HmfH gene is integrated in the chromosome of the transformant of Example 1 and the HMFO gene is integrated in the chromosome of the transformant of Example 4 without affecting their enzyme activity and can successfully convert HMF to FDCA.

1.2. Effect of the Initial Concentration of HMF on the Conversion of HMF to HMF Derivatives After confirming that the transformants of Example 1 and Example 4 can successfully convert HMF to FDCA at the initial concentration of 50 mM, the initial concentration of HMF is further increased to discuss the effect of different initial concentrations of HMF on the conversion of HMF to its derivatives. The transformants of Example 1 and Example 4 are respectively inoculated into the reaction substrate including the initial concentrations of HMF at 50 mM, 60 mM, 70 mM, 80 mM, 90 mM and 100 mM, and fermented at 30° C. Samples are taken at 24 hours of fermentation, and the content of HMF and other subsequent derivatives in the fermented substance are analyzed by HPLC. In addition, Samples are taken at 0, 3, 6, 12, and 24 hours of fermentation to measure $OD_{600}$ value.

Figure 8A:
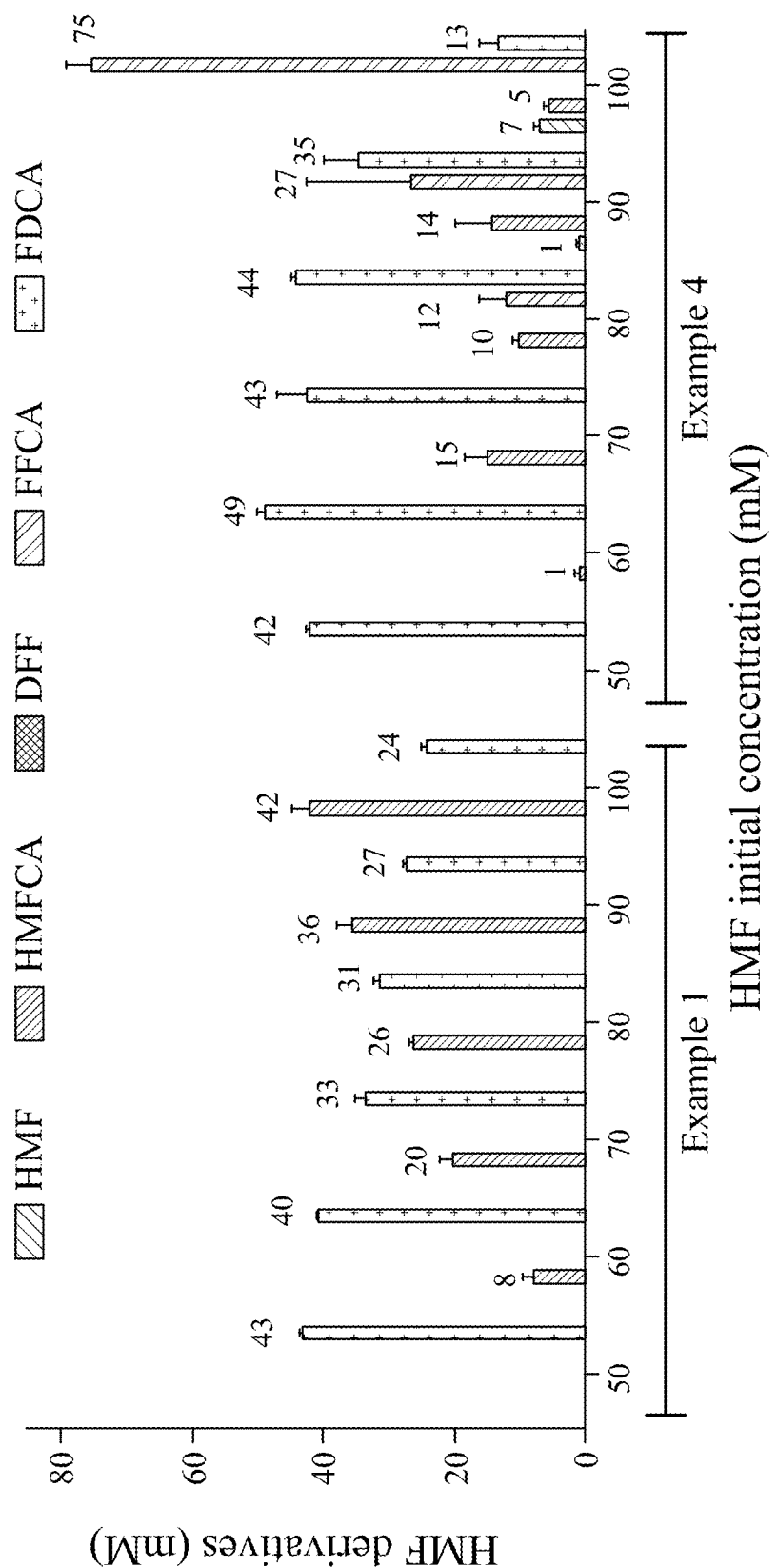
FIG. 8A shows analytical results of the efficiency of the transformants of Example 1 and Example 4 in converting 5-hydroxymethylfurfural to 2,5-furandicarboxylic acid under different initial concentrations of 5-hydroxymethylfurfural.
Figure 8B:
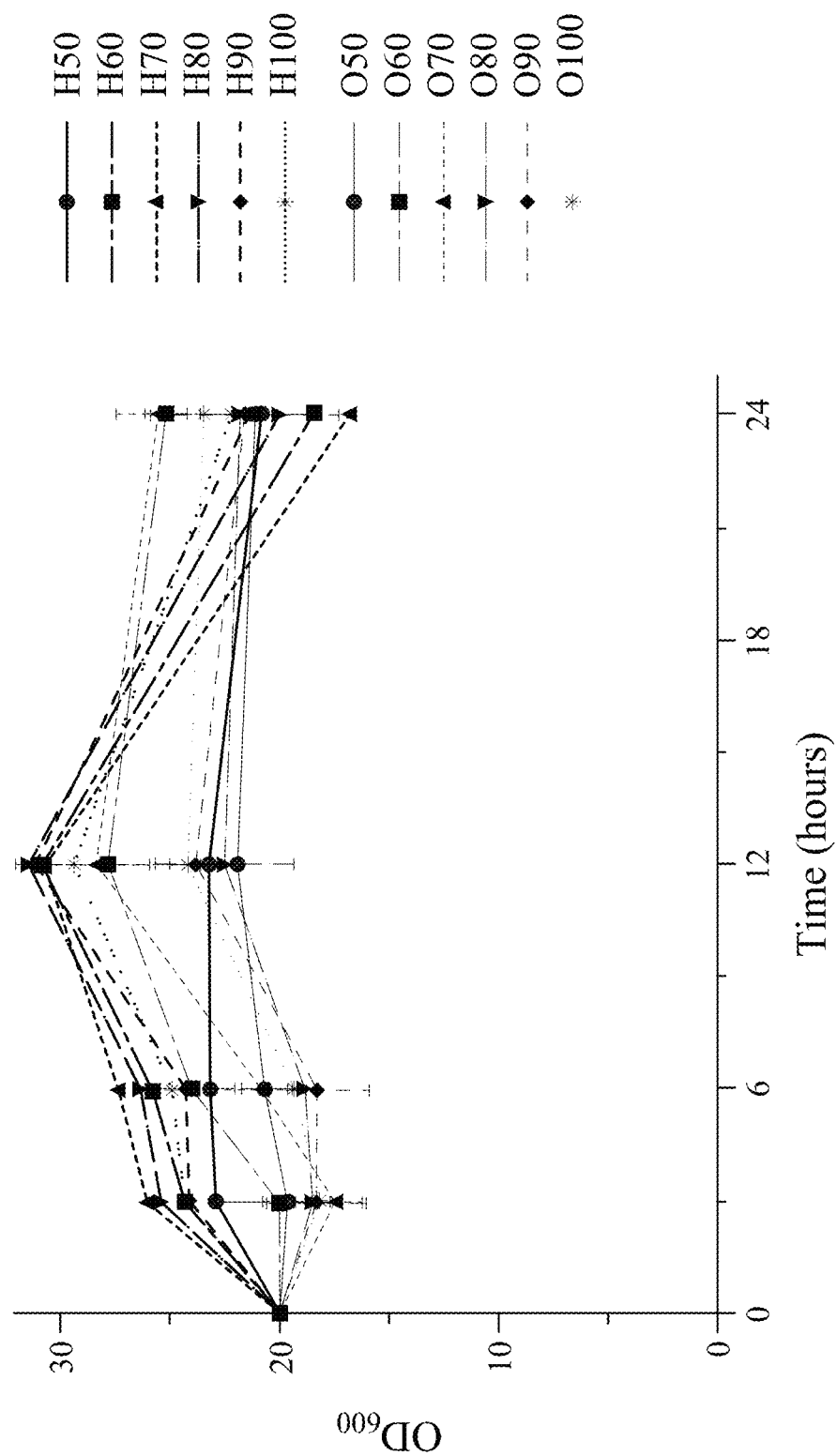
FIG. 8B shows $OD_{600}$ values of the transformants of Example 1 and Example 4 under different initial concentrations of 5-hydroxymethylfurfural for 24 hours.

Please refer to FIGS. 8A and 8B. FIG. 8A shows analytical results of the efficiency of the transformants of Example 1 and Example 4 in converting HMF to FDCA under different initial concentrations of HMF, and FIG. 8B shows $OD_{600}$ values of the transformants of Example 1 and Example 4 under different initial concentrations of HMF for 24 hours, wherein H50, H60, H70, H80, H90 and H100 represent the transformant of Example 1 fermented at different initial concentrations of HMF, and O50, O60, O70, O80, O90 and O100 represent the transformant of Example 4 fermented at different initial concentrations of HMF.

In FIG. 8A, in the group inoculated with the transformant of Example 1, increasing the initial concentration of HMF increases accumulation of intermediate product HMFCA, which will reduce the conversion of FDCA. When the initial concentration of HMF is 50 mM, HMF can be completely converted to 43 mM FDCA. However, the converted FDCA concentration gradually decreased to 24 mM as the initial concentration of HMF increased. At the same time, the accumulation of HMFCA will gradually increase from 0 mM to 42 mM as the initial concentration of HMF increased. In the group inoculated with the transformant of Example 4, FDCA concentration (49 mM) can be reached when the initial concentration of HMF is 60 mM. However, when the initial concentration of HMF is increased from 70 mM to 100 mM, the accumulations of intermediate products HMFCA and FFCA are increased or causing part of HMF to be converted into derivatives, which will reduce the conversion of FDCA.

In FIG. 8B, the growths of the transformants of Example 1 and Example 4 under different initial concentrations of HMF are good within 24 hours, indicating that increasing the initial concentration of HMF would not affect the growths of the transformants of Example 1 and Example 4.

1.3. Example 5

The above results indicate that the transformants of Example 1 and Example 4 can convert HMF to FDCA. However, increasing the initial concentration of HMF increases accumulation of intermediate products (HMFCA and/or FFCA), which cannot be convert to FDCA. To further optimize the results of the preparation method for 2,5-furandicarboxylic acid of the present disclosure, a transformant for producing 2,5-furandicarboxylic acid with the HmfH gene and the HMFO gene is prepared, and is used to produce FDCA by the preparation method for 2,5-furandicarboxylic acid of the present disclosure.

Firstly, the constructed pRedSpCas9 plasmid is transformed into the *Pseudomonas putida* by electroporation, and cultured in LB medium including gentamicin to select the transformant that successfully transformed the RedCas expression plasmid. Then the exogenous gene expression plasmid with the HmfH gene including the nucleic acid sequence of SEQ ID NO: 1 and the HMFO gene including the nucleic acid sequence of SEQ ID NO: 2 is transformed into the transformant by electroporation to obtain the transformant of Example 5 (with the HmfH gene and the HMFO gene). The mechanism of the insertion of the HmfH gene and the HMFO gene into the transformant of Example 5 is as described above, and will not be repeated here. The transformant of Example 5 is inoculated into the reaction substrate including the initial concentrations of HMF at 50 mM, 60 mM, 70 mM, 80 mM, 90 mM and 100 mM, and fermented at 30° C. Samples are taken at 24 hours of fermentation, and the content of HMF and other subsequent derivatives in the fermented substance are analyzed by HPLC.

Figure 9:
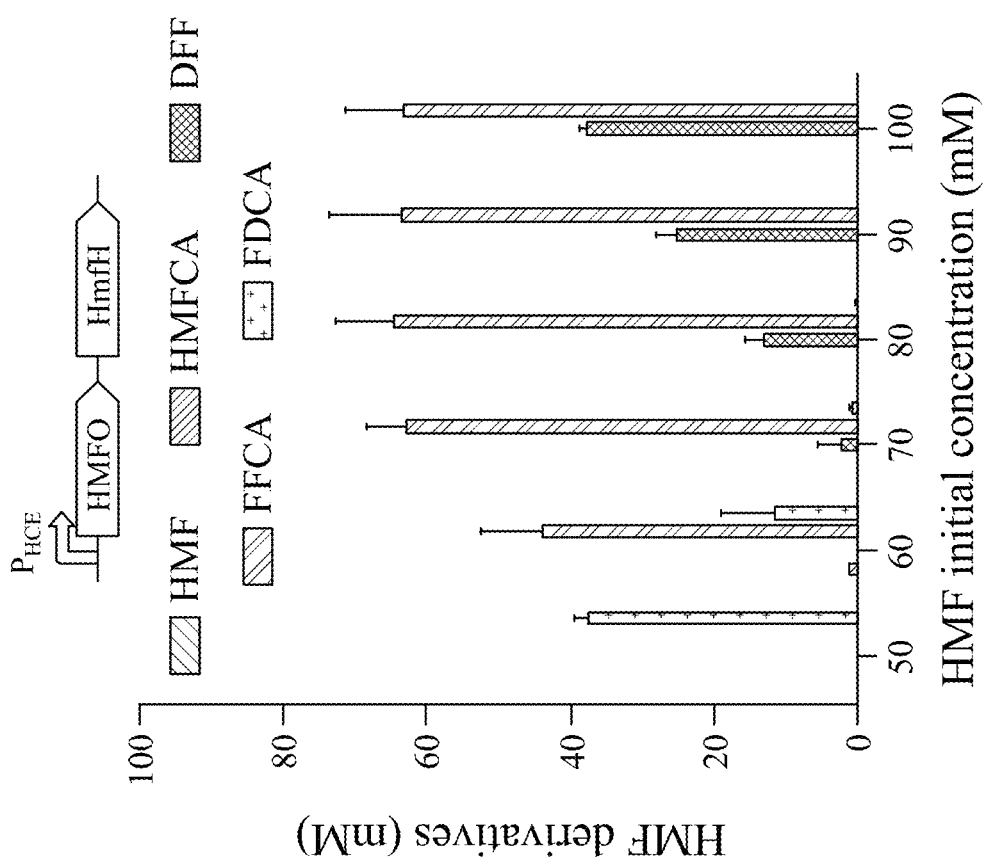
FIG. 9 shows an analytical result of the efficiency of the transformant of Example 5 in converting 5-hydroxymethylfurfural to 2,5-furandicarboxylic acid.

Please refer to FIG. 9, which shows an analytical result of the efficiency of the transformant of Example 5 in converting HMF to FDCA. In FIG. 9, the transformant of Example 5 can successfully convert HMF to FDCA at the initial concentration of 50 mM. However, HMF is converted into intermediate products HMFCA, FFCA and DFF as the initial concentration of HMF increased, which will reduce the conversion of FDCA.

1.4. Effect of Addition of Manganese Dioxide and/or Calcium Carbonate on the Conversion of HMF to HMF Derivatives To further optimize the results of the preparation method for 2,5-furandicarboxylic acid of the present disclosure, manganese dioxide and/or calcium carbonate are added to the reaction substrate, and then the transformants of Example 1 or Example 4 is respectively inoculated into the reaction substrate to produce FDCA.

A reaction substrate including 100 mM HMF, a reaction substrate including 100 mM HMF and 0.5 g/L manganese dioxide, a reaction substrate including 100 mM HMF and 30 g/L calcium carbonate, and a reaction substrate including 100 mM HMF, 0.5 g/L manganese dioxide and 30 g/L calcium carbonate are prepared, respectively. The transformants of Example 1 and Example 4 are respectively inoculated into the prepared reaction substrate, and fermented at 30° C. Samples are taken at 24 hours of fermentation, and the content of HMF and other subsequent derivatives in the fermented substance are analyzed by HPLC. Please refer to Table 1, which is the transformant and the addition amount of manganese dioxide and/or calcium carbonate used in Examples 6 to 13 of the present disclosure.

TABLE 1

| Example | Transformant | addition amount of manganese dioxide | addition amount of calcium carbonate |
|---|---|---|---|
| Example 6 | Example 1 | — | — |
| Example 7 | Example 1 | 0.5 g/L | — |
| Example 8 | Example 1 | — | 30 g/L |
| Example 9 | Example 1 | 0.5 g/L | 30 g/L |
| Example 10 | Example 4 | — | — |
| Example 11 | Example 4 | 0.5 g/L | — |

TABLE 1-continued

| Example | Transformant | addition amount of manganese dioxide | addition amount of calcium carbonate |
|---|---|---|---|
| Example 12 | Example 4 | — | 30 g/L |
| Example 13 | Example 4 | 0.5 g/L | 30 g/L |

Figure 10:
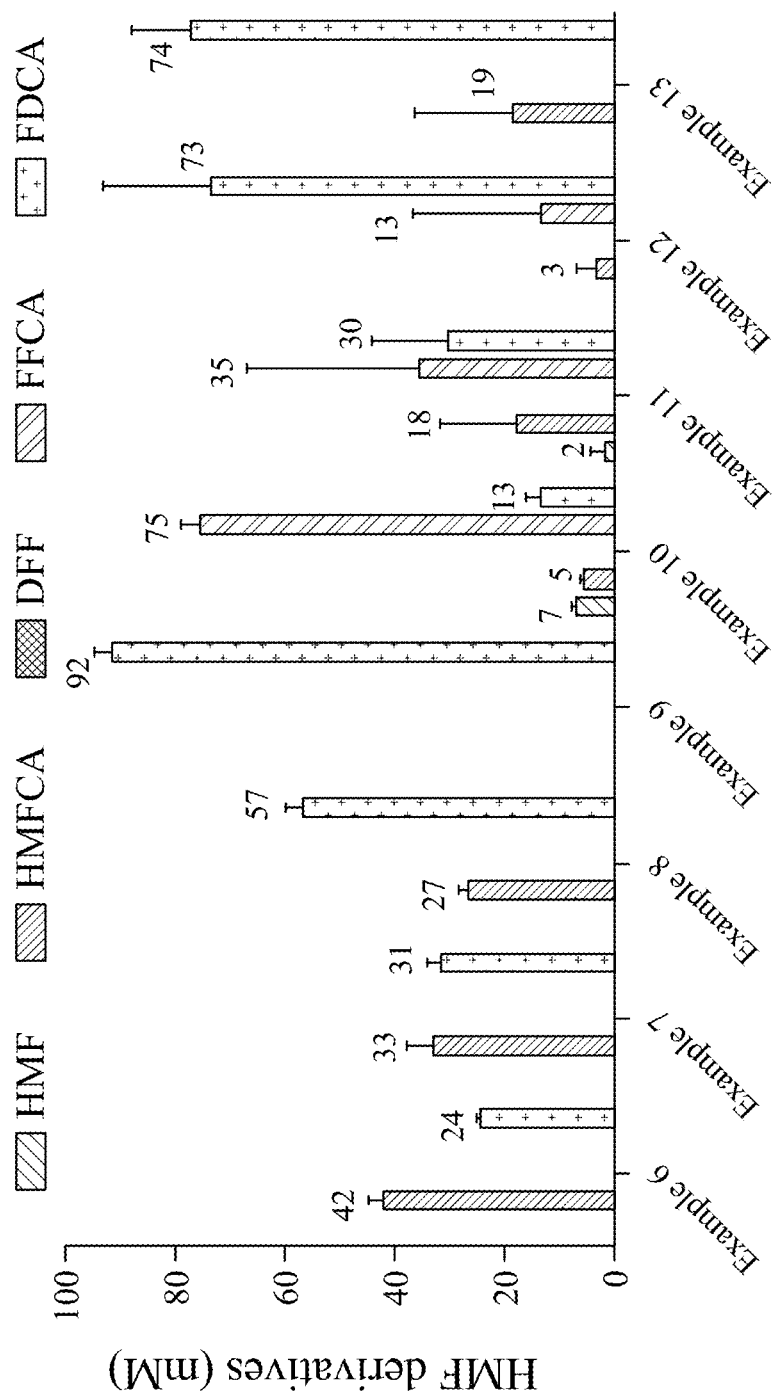
FIG. 10 shows analytical results of the efficiency of the transformants of Example 6, Example 7, Example 8, Example 9, Example 10, Example 11, Example 12 and Example 13 in converting 5-hydroxymethylfurfural to 2,5-furandicarboxylic acid.

Please refer to FIG. 10, which shows analytical results of the efficiency of the transformants of Example 6, Example 7, Example 8, Example 9, Example 10, Example 11, Example 12 and Example 13 in converting HMF to FDCA. When the transformant of Example 1 is used for fermentation, 100 mM HMF is converted to 24 mM FDCA and 42 mM HMFCA in Example 6 without adding manganese dioxide or calcium carbonate. In Example 7 where manganese dioxide is added, the concentration of FDCA converted from HMF is increased to 31 mM, and the concentration of HMFCA is decreased to 33 mM. In Example 8 where calcium carbonate is added, the concentration of FDCA converted from HMF is increased to 57 mM, and the concentration of HMFCA is decreased to 27 mM. In Example 9 where manganese dioxide and calcium carbonate are simultaneously added, HMF can be completely converted to FDCA, and the concentration of FDCA can reach 92 mM. When the transformant of Example 4 is used for fermentation, 100 mM HMF is converted to 13 mM FDCA, 5 mM HMFCA and 75 mM FFCA in Example 10 without adding manganese dioxide or calcium carbonate. In Example 11 where manganese dioxide is added, the concentration of FDCA converted from HMF is increased to 30 mM, the concentration of HMFCA is increased to 18 mM, and the concentration of FFCA is decreased to 35 mM. In Example 12 where calcium carbonate is added, the concentration of FDCA converted from HMF is increased to 73 mM, the concentration of HMFCA is decreased to 3 mM, and the concentration of FFCA is decreased to 13 mM. In Example 13 where manganese dioxide and calcium carbonate are simultaneously added, the concentration of FDCA converted from HMF can reach 74 mM and the concentration of HMFCA is 19 mM. The results indicate that the addition of manganese dioxide and/or calcium carbonate can improve enzyme activity.

1.5. Effect of Addition of Manganese Dioxide and/or Calcium Carbonate and the Initial Concentration of HMF on the Productivity of FDCA After proving that the addition of manganese dioxide and/or calcium carbonate can optimize the FDCA production of the preparation method for 2,5-furandicarboxylic acid of the present disclosure, the effect of different initial concentrations of HMF on the conversion of HMF to derivatives is further discussed when manganese dioxide and/or calcium carbonate are added.

The transformant of Example 1 is respectively inoculated into reaction substrates including 0.5 g/L of manganese dioxide, 30 g/L of calcium carbonate and different initial concentrations of HMF as Example 14, in which the initial concentrations of HMF are 125 mM, 150 mM, 175 mM, 200 mM, 225 mM and 250 mM, respectively. The fermentation is performed at 30° C. Samples are taken at the 24th hour of fermentation, the content of HMF and other subsequent derivatives in the fermented substance are analyzed by HPLC, and the FDCA production rate is calculated.

Figure 11:
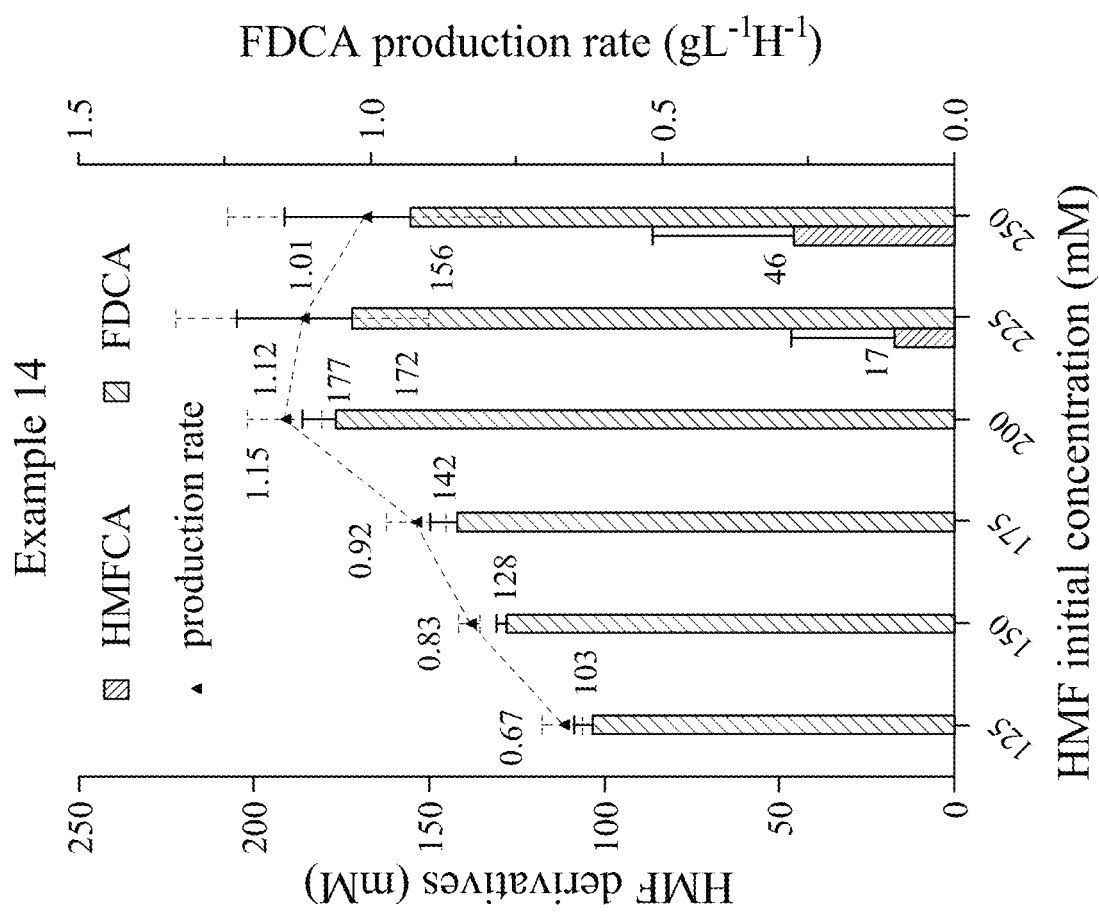
FIG. 11 shows an analytical result of the efficiency of the transformant of Example 14 in converting 5-hydroxymethylfurfural to 2,5-furandicarboxylic acid.

Please refer to FIG. 11, which shows an analytical result of the efficiency of the transformant of Example 14 in converting HMF to FDCA. When the transformant of Example 1 is used for fermentation and manganese dioxide and calcium carbonate are simultaneously added into the reaction substrate, the concentration of FDCA converted from HMF is the highest at the initial concentration of HMF of 200 mM. The concentration of FDCA can reach 177 mM and the FDCA production rate is 1.15 g/L/h.

1.6. Examples 15-17

Figure 12A:
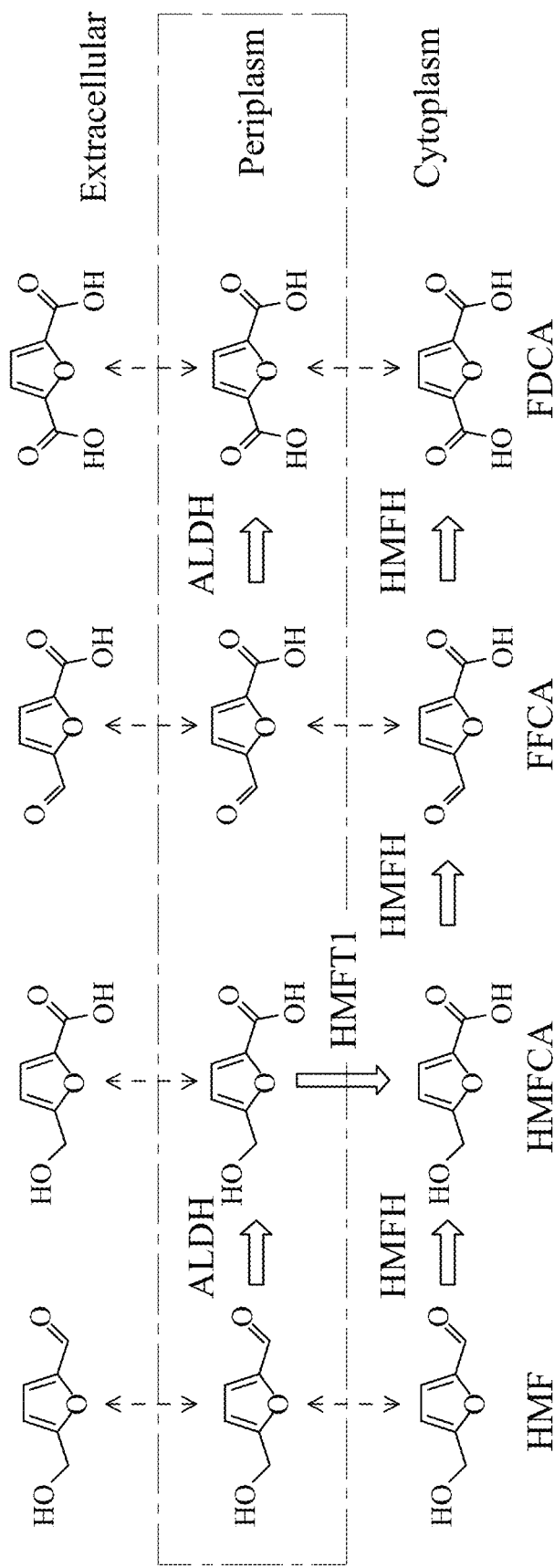
FIG. 12A is a schematic view showing reaction pathway for the transformants of Example 15, Example 16 and Example 17 to convert 5-hydroxymethylfurfural to 2,5-furandicarboxylic acid.

Please refer to FIG. 12A, which is a schematic view showing reaction pathway for the transformants of Example 15, Example 16 and Example 17 to convert HMF to FDCA. As shown in the results of Example 14 in paragraphs [0076] to [0079], when the initial concentration of HMF is 250 mM, the accumulation of HMFCA is increased. It is reported that the *Pseudomonas putida* S12 lacks HMFCA transporter, and HMFT1 is a membrane bound transporter that can transport HMFCA from the medium into cytoplasm and is absent in the *Pseudomonas putida* S12. In order to further increase the production of HMF-converted FDCA, transformants of Example 15, Example 16, and Example 17 with the HmfH gene and the HmfT1 gene are further prepared, so that the co-expression of HmfT1 and HmfH can reduce the accumulation of HMFCA in the medium and increase the production of FDCA.

Constitutive promoters ($P_{Gm}$, $P_{Tet}$, and $P_C$) with different transcriptional strengths are used as the promoters for the transcription of the HmfT1 gene to construct exogenous gene expression plasmids with the HmfH gene including the nucleic acid sequence of SEQ ID NO: 1 and the HmfT1 gene including the nucleic acid sequence of SEQ ID NO: 35. When preparing the transformants of Example 15 to Example 17, the constructed pRedSpCas9 plasmid is transformed into the *Pseudomonas putida* by electroporation, and cultured in LB medium including gentamicin to select the transformant that successfully transformed the RedCas expression plasmid. Then the exogenous gene expression plasmids with the HmfH gene and the HmfT1 gene using different promoters are respectively transformed into the transformant by electroporation to obtain the transformant of Example 15 (with $P_{Gm}$ promoter), the transformant of Example 16 (with $P_{Tet}$ promoter) and the transformant of Example 17 (with $P_C$ promoter). The mechanism of the insertion of the HmfH gene and the HmfT1 gene into the transformants of Example 15 to Example 17 is as described above, and will not be repeated here. The transformants of Example 15, Example 16 and Example 17 are respectively inoculated into the reaction substrate including 250 mM HMF, 0.5 g/L manganese dioxide and 30 g/L calcium carbonate, and fermented at 30° C. Samples are taken at 24 hours of fermentation, and the content of HMF and other subsequent derivatives in the fermented substance are analyzed by HPLC.

Figure 12B:
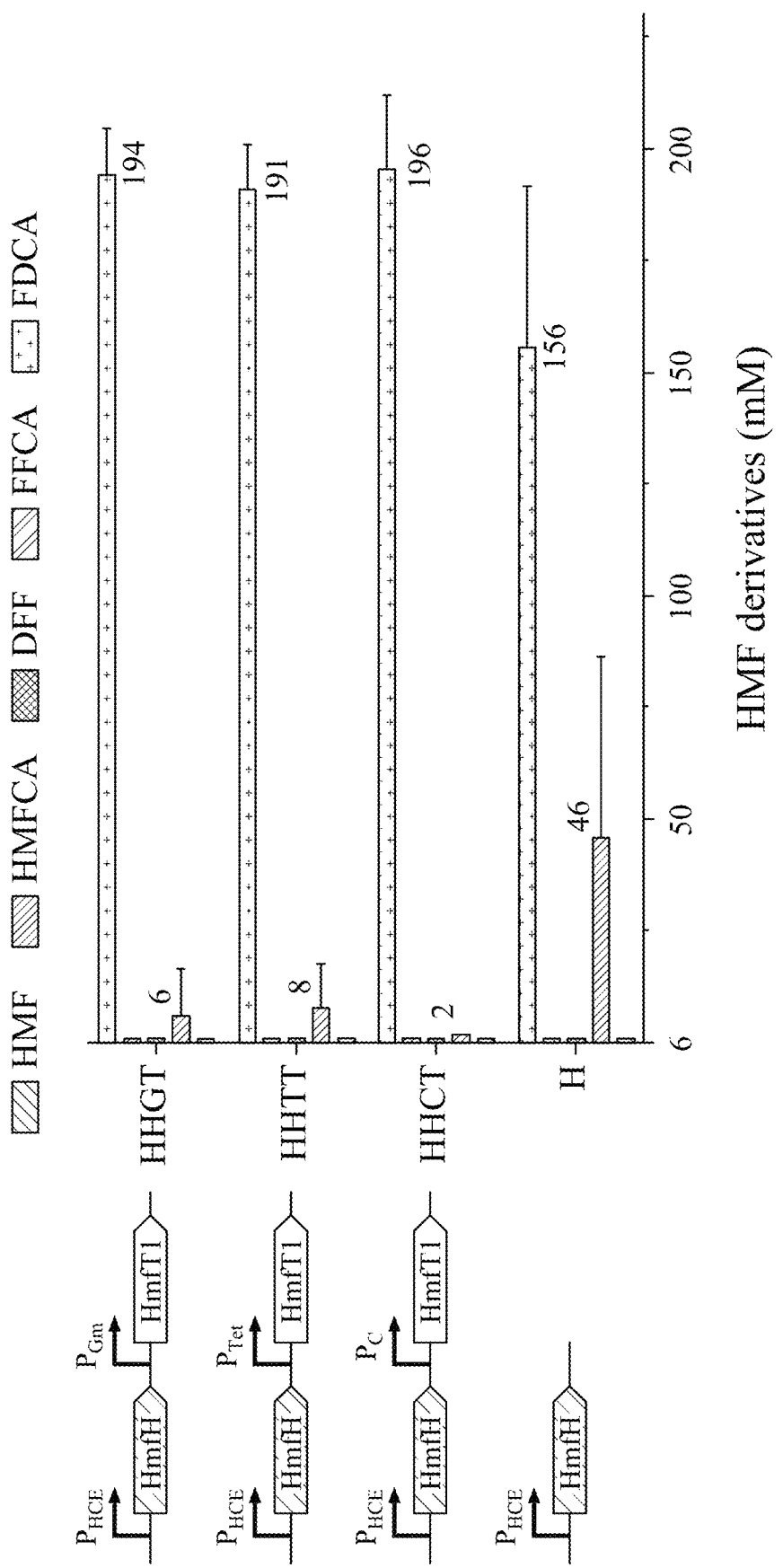
FIG. 12B shows analytical results of the efficiency of the transformants of Example 15, Example 16 and Example 17 in converting 5-hydroxymethylfurfural to 2,5-furandicarboxylic acid.

Please refer to FIG. 12B, which shows analytical results of the efficiency of the transformants of Example 15, Example 16 and Example 17 in converting HMF to FDCA. In FIG. 12B, by co-expressing HmfT1 with HmfH on the cell membrane, the transformants of Example 15 to Example 17 can convert 250 mM HMF to 190 mM or more FDCA regardless of the promoter used. In particular, the transformant of Example 17 with the $P_C$ promote for the transcription of the HmfT1 gene can convert 250 mM HMF to 196 mM FDCA within 24 hours, and only 2 mM HMFCA is present in the medium. In addition, compared with the transformant of Example 1, the transformant of Example 17 can also increase the FDCA production rate (1.27 g/L/h) under the same fermentation condition.

In summary, the transformant for producing 2,5-furandicarboxylic acid of the present disclosure can stably produce 2,5-furandicarboxylic acid and be cultured at low-cost culture, which integrates at least one exogenous gene in the chromosome of the Pseudomonas putida, and the at least one exogenous gene can translate the enzyme that converts 5-hydroxymethylfurfural to 2,5-furandicarboxylic acid. Therefore, the transformant can stably express enzymes without adding additional antibiotics to maintain enzyme performance, so it can be used as a stable and efficient biological production plant. The preparation method for 2,5-furandicarboxylic acid of the present disclosure uses the transformant for producing 2,5-furandicarboxylic acid of the present disclosure, which can efficiently convert 5-hydroxymethylfurfural in the reaction substrate into 2,5-furandicarboxylic acid, and antibiotics and expensive inducers do not be added in the culture process. In addition, the production rate of 2,5-furandicarboxylic acid can be optimized with the addition of manganese dioxide and/or calcium carbonate. The preparation method for 2,5-furandicarboxylic acid of the present disclosure is suitable for industrialization under the consideration of cost, and has application potential for relevant markets and industrial utilization.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A transformant for producing 2,5-furandicarboxylic acid, comprising:
a host cell, wherein the host cell is *Pseudomonas putida*; and at least one exogenous gene, wherein the at least one exogenous gene is a HmfH gene comprising the nucleic acid sequence of SEQ ID NO: 1 or a HMFO gene comprising the nucleic acid sequence of SEQ ID NO: 2, and the at least one exogenous gene is integrated in a chromosome of the host cell.

2. The transformant for producing 2,5-furandicarboxylic acid of claim 1, wherein the at least one exogenous gene is integrated in the chromosome of the host cell using a gene editing system, and the gene editing system comprises:
a RedCas expression plasmid, which successively comprises a first replication origin, a first antibiotic resistance gene, a λ-Red expression cassette and a Cas expression cassette, wherein the first replication origin comprises the nucleic acid sequence of SEQ ID NO: 8, the λ-Red expression cassette comprises a first promoter, a Gam gene, a Bet gene and an Exo gene, and the Cas expression cassette comprises a second promoter and a Cas gene; and
an exogenous gene expression plasmid, which successively comprises a second replication origin, a left homology arm, a second antibiotic resistance gene, an exogenous gene expression cassette, a right homology arm and a gRNA cassette, wherein the exogenous gene expression cassette comprises a third promoter and the at least one exogenous gene, the gRNA cassette comprises a fourth promoter and a gRNA sequence, and the gRNA sequence is composed of a spacer and a scaffold;
wherein the left homology arm and the right homology arm compose a homology region, a sequence of the homology region is homologous to a first specific sequence of a chromosome of the *Pseudomonas putida*, a sequence of the spacer is homologous to a second specific sequence of the chromosome of the *Pseudomonas putida*, and the first antibiotic resistance gene and the second antibiotic resistance gene are different.

3. The transformant for producing 2,5-furandicarboxylic acid of claim 2, wherein the Cas gene comprises the nucleic acid sequence of SEQ ID NO: 16, the nucleic acid sequence of SEQ ID NO: 17 or the nucleic acid sequence of SEQ ID NO: 18.

4. The transformant for producing 2,5-furandicarboxylic acid of claim 2, wherein a number of the at least one exogenous gene is two, and the two exogenous gene are the same or different.

5. The transformant for producing 2,5-furandicarboxylic acid of claim 1, wherein when the at least one exogenous gene is the HmfH gene, the at least one exogenous gene further comprises a HmfT1 gene comprising the nucleic acid sequence of SEQ ID NO: 35.

6. The transformant for producing 2,5-furandicarboxylic acid of claim 1, wherein the *Pseudomonas putida* is *Pseudomonas putida* S12.

7. A preparation method for 2,5-furandicarboxylic acid, comprising:
   providing a reaction substrate, wherein the reaction substrate comprises 5-hydroxymethylfurfural; and
   performing a fermentation step, wherein the reaction substrate is inoculated with the transformant for producing 2,5-furandicarboxylic acid of claim 1, then is cultured at a fermentation temperature for a fermentation time to obtain a fermented substance, and the fermented substance comprises the 2,5-furandicarboxylic acid.

8. The preparation method for 2,5-furandicarboxylic acid of claim 7, wherein an initial concentration of 5-hydroxymethylfurfural in the reaction substrate is 50 mM to 250 mM.

9. The preparation method for 2,5-furandicarboxylic acid of claim 7, wherein the fermentation temperature is 30° C., and the fermentation time is 24 hours.

10. The preparation method for 2,5-furandicarboxylic acid of claim 7, wherein the reaction substrate further comprises manganese dioxide and/or calcium carbonate.

11. The preparation method for 2,5-furandicarboxylic acid of claim 10, wherein the addition amount of manganese dioxide in the reaction substrate is 0.1 g/L to 1 g/L.

12. The preparation method for 2,5-furandicarboxylic acid of claim 10, wherein the addition amount of calcium carbonate in the reaction substrate is 5 g/L to 60 g/L.

* * * * *

SEQUENCE LISTING

<160> NUMBER OF SEQ ID NOS: 35

<210> SEQ ID NO 1
<211> LENGTH: 1737
<212> TYPE: DNA
<213> ORGANISM: Artificial Sequence
<220> FEATURE:
<223> OTHER INFORMATION: HmfH gene

<400> SEQUENCE: 1

```
atggacaccc cgcgcgagcg tttcgactac gtcattgtcg gcggcggtag cgccggctgc      60
gtgttggcga accgtctgtc gcaggacccc gccatccgcg tggccttgat tgaggccggc     120 gtggatacc  cgcccgatgc cgtgcccgcg gaaatcctgg actcgtaccc gatgccgctg     180
ttcttcggcg atcgctacat ctggcccctcg ctgcaagcgc gcgccgtggc cggcggccgc     240
agcaaggtct atgagcaagg ccgcgtcatg ggcggtggct cgagcatcaa tgtgcaggcc     300
gccaaccgcg gcctgccgcg cgactacgat gaatgggccg cgagcggcgc cagcggctgg     360
agctggcagg atgtgttgcc ctactttcgt cacctggaac gcgacgtgga ctacggcaac     420
agccccctgc acggtagcca cggcccggtg ccgatccgcc gcattttgcc ccaggcctgg     480
ccgccgttct gcacggaatt cgcccatgcc atgggccgct cgggtttgtc ggccctggcc     540
gaccagaacg ccgagttcgg tgacggttgg ttcccggcgg ccttcagcaa cctggacgac     600
aaacgcgtca gcaggcgat  cgcgtacctg gatgccgaca cccgccgtcg tgccaacctg     660
cgcatctacg ccgagaccac cgtgcgtaag ctggtcgtgt cgggccgtga agcgcgtggc     720
gtgatcgcca tgcgcgcgga tggttcgcgt ctggccctga tgcgggtga  agtcatcgtg     780 agcgccggcg ccctgcagtc gccggccatc ttgatgcgcg ccggcatcgg tgatgccggc     840
gcgttgcaag ccctgggcat cgaggtggtg gccgatcgtc ctggtgtcgg ccgtaatttg     900
caggaccacc cggcgctgac cttctgccag ttcctggcgc cccagtaccg tatgccgttg     960
tcgcgccgcc gtgccagcat gaccgccgcc cgctttagca gcggcgtgcc gggcggcgag    1020
gccagcgata tgtacctgtc gagctcgacc cgtgccggct ggcacgccct gggcaatcgc    1080
ctgggcttgt ttttcttgtg gtgcaaccgc ccgttcagcc gcggtcaggt gagcttggcc    1140
ggcgcgcagc cggacgtgcc gcccatggtc gagctgaacc tgctggacga tgaacgtgac    1200
ctgcgccgca tggtggccgg cgtgcgtaaa ctggtccaga tcgtgggtgc gtcggccttg    1260
```

```
caccaacatc ctggtgattt cttcccggcc accttctcgc cccgtgtgaa agccctgtcg    1320
cgcgtgagcc gtggcaatgt gctgctgacc gaactgctgg gtgccgtcct ggacgtgagc    1380
ggtccgttgc gccgtagcct gatcgcccgt tcgtgaccg gcggcgccaa cttggccagc     1440
ctgctgacgg acgaaagcgc cctggagggc ttcgtgcgtc agtcggtgtt cggcgtgtgg    1500
catgcctcgg gcacctgtcg catgggtgcc cacgccgatc gcagcgccgt caccgacgcc    1560
gccggccgcg tccacgatgt gggccgcctg cgtgtgatcg acgccagcct gatgccccgc    1620
ctgccgaccg ccaacaccaa catcccgacc atcatgctgg ccgagaagat cgcggacacc    1680
atgcaggccg agcgccgcgc cgtgcgcccg ccagcagcg aagtcgccca tcccagc       1737
```

<210> SEQ ID NO 2
<211> LENGTH: 1611
<212> TYPE: DNA
<213> ORGANISM: Artificial Sequence
<220> FEATURE:
<223> OTHER INFORMATION: HMFO gene

<400> SEQUENCE: 2

```
atgacggaca ccatcttcga ttacgtgatc gtgggcggcg gcaccgcggg ttcggtgctg     60
gcgaaccgct tgagcgcccg cccggaaaac cgcgtgttgc tgatcgaggc cggcatcgat    120
accccggaaa acaacatccc gccggagatt cacgacggct tgcgcccgtg gctgccccgc    180
ctgagcggtg acaagttctt ctggcccaac ctgaccatcc accgtgcggc cgagcacccg    240
ggcatcaccc gcgagccgca gttctatgaa cagggtcgcc tgttgggcgg cggtagcagc    300
gtgaacatgg tggtgagcaa ccgtggtctg ccgcgtgact acgacgaatg caggccctg     360 ggcgcggacg gttgggactg caggcgtg ctgccgtatt tcatcaagac cgagcgcgac     420
gccgactacg gcgatgaccc cttgcatggc aacgccggcc ccattccgat cggccgtgtg    480
gacagccgtc actggagcga tttcaccgtg gcggccaccc aggccctgga agccgccggc    540
ttgcccaaca tccacgatca gaacgcccgc ttcgatgacg gctacttccc gccggccttt    600
acgctgaagg gcgaggagcg tttcagcgcc gccgcggtt atctggatgc ctcggtgcgc    660
gtgcgcccga acctgtcgtt gtggaccgag agccgcgtct tgaaactgct gaccaccggt    720
aacgcgatca ccggtgtcag cgtgctgcgt ggccgcgaga ccttgcaggt gcaggcgcgt    780
gaggtgatct tgaccgccgg tgccttgcag tcgccggcca ttctgctgcg caccggtatc    840
ggtcccgcgg ccgatctgca tgccttgggc atcccgtgt tggccgatcg cccgggtgtc    900
ggccgcaact tgtgggaaca tagcagcatc ggcgtggtcg cgccgttgac ggaacaggcc    960
cgcgccgatg ccagcaccgg caaggccggt agccgtcacc aactgggcat ccgcgccagc   1020
tcgggcgtgg accccgccac ccgtcggat ctgttcctgc acatcggcgc cgaccccgtg    1080
agcggtctgg ccagcgccgt gttctgggtg aacaagccgt cgagcaccgg ctggctgaag   1140
ctgaaagatg cggaccgtt cagctatccc gacgtgact tcaatctgtt gagcgatccc     1200
cgcgacttgg ccgttgaa ggccggcctg cgcctgatca cccattactt cgccgcgccc     1260
tcgttggcca gtatggctt ggcgctggcc ttgagccgtt cgccgcccc gcaaccgggc     1320 ggcccgctgc tgaacgacct gttgcaggac gaggccgccc tggagcgtta cctgcgcacc    1380
aacgtgggcg gtgtgtggca cgccagcggt accgcccgca tcggccgcgc cgatgatagc    1440
caggccgtgg tggacaaggc cggccgtgtg tacggcgtga ccggcctgcg cgtggccgac    1500
gccagcatta tgccgaccgt gccgaccgcg aacaccaatt tgcccaccct gatgctggcc    1560
gagaaaatcg ccgacgccat cctgacgcag gcccaccacc accaccacca c            1611
```

<210> SEQ ID NO 3
<211> LENGTH: 1722
<212> TYPE: DNA
<213> ORGANISM: Artificial Sequence
<220> FEATURE:
<223> OTHER INFORMATION: AAO gene

<400> SEQUENCE: 3

| | | | | | |
|---|---|---|---|---|---|
| atggccgatt | tcgactacgt | cgtggttggc | gccggcaacg | ccggcaacgt | ggtcgccgcc | 60 |
| cgtctcacgg | aggacccgga | cgtctccgtt | ctggttctgg | aagccggcgt | ttcggacgaa | 120 |
| aacgtgctgg | gtgctgaggc | accgctcctg | gccccgggcc | tggtcccgaa | ctccatcttc | 180 |
| gactggaact | acaccaccac | cgcgcaggcc | ggctacaatg | gtcgctccat | tgcctatccc | 240 |
| cgcggccgca | tgctgggcgg | tagctcctcc | gtgcactaca | tggtgatgat | gcgcggctcc | 300 |
| accgaggact | cgatcgcta | cgctgccgtt | accggcgacg | agggctggaa | ctgggacaac | 360 |
| attcagcagt | tcgtccgtaa | aaacgagatg | gtcgtcccgc | cggccgacaa | ccacaacacc | 420 |
| tcgggcgaat | tcatcccggc | cgtccacggc | accaacggta | gcgtcagcat | ttcgctcccg | 480 |
| ggtttcccaa | cccctctgga | tgaccgtgtc | ctggccacca | ctcaggagca | gagcgaagaa | 540 |
| ttcttcttca | acccggacat | gggcaccggc | cacccgctgg | gcatctcctg | gtcgatcgcc | 600 |
| agcgtcggca | acgccagcg | ttccagctcg | agcaccgctt | acctgcgccc | ggcacagtct | 660 |
| cgtccgaacc | tgtcggtgct | gatcaacgcc | caggtcacca | aactggttaa | cagcggtacc | 720 |
| accaatggcc | tgcctgcttt | ccgctgcgtg | gagtacgccg | aacaggaggg | cgcgccgacc | 780 |
| accactgttt | gcgccaagaa | ggaggtcgtt | ctgtcggccg | gcagcgtcgg | cacccctatc | 840 |
| ctgctgcaac | tgtccggtat | cggcgacgag | aacgatctct | cctctgtcgg | catcgatacc | 900 |
| atcgttaaca | acccgtcggt | gggccgtaac | ctgagcgacc | acctcctgct | gccagctgcc | 960 |
| ttcttcgtca | actcgaacca | gaccttcgac | aacatcttcc | gtgattcctc | cgagttcaac | 1020 |
| gtggacctgg | accagtggac | caacacccgc | accggccccc | tgaccgccct | gatcgcgaac | 1080 |
| cacctggctt | ggctgcgtct | gccttccaac | tcgagcatct | tccaaacctt | tcctgacccg | 1140 |
| gcggctggcc | ctaacagcgc | ccactgggaa | accatcttca | gtaaccaatg | gttccaccct | 1200 |
| gccatcccgc | gcccagatac | cggttccttc | atgtccgtca | ccaacgcgct | gatctccccg | 1260 |
| gtcgcgcgcg | gcgacatcaa | gctggccacc | tcgaacccat | tcgacaagcc | gctgatcaac | 1320 |
| ccgcagtacc | tgtccactga | attcgacatc | ttcaccatga | tccaggctgt | gaaatcgaac | 1380 |
| ctgcgttttcc | tgagcggcca | ggcctgggca | gacttcgtca | tccgtccgtt | cgacccgcgc | 1440 |
| ctgcgcgacc | caacggacga | cgccgccatc | gaatcgtaca | tccgcgataa | cgcgaacacc | 1500 |
| atcttccatc | cagtgggtac | tgcctcgatg | tccccacgtg | gcgcctcgtg | gggcgttgtg | 1560 |
| gacccagacc | tgaaggttaa | gggcgttgac | ggcctgcgta | ttgttgatgg | ttccatcctg | 1620 |
| ccgttcgccc | ctaacgctca | cacccagggc | ccgatctacc | tggtcggcaa | acagggtgct | 1680 |
| gatctgatca | aagctgatca | gcaccaccac | caccaccact | ga | | 1722 |

<210> SEQ ID NO 4
<211> LENGTH: 924
<212> TYPE: DNA
<213> ORGANISM: Artificial Sequence
<220> FEATURE:
<223> OTHER INFORMATION: CPO gene

<400> SEQUENCE: 4

-continued

| | |
|---|---|
| atggaaccgg gctcgggcat cggctatccg tacgataaca acaccctgcc gtatgtggcc | 60 |
| ccgggcccga ccgactcccg tgctccgtgc ccggccctga acgctctggc taaccacggt | 120 |
| tacatcccgc acgacggtcg cgctatctcg cgcgagaccc tgcaaaacgc cttcctgaac | 180 |
| cacatgggca tcgcgaattc ggttatcgaa ctggccctca ccaacgcctt cgtcgtatgc | 240 |
| gagtacgtta ctggctccga ctgcggtgac tcgctggtta acctgactct gctggctgaa | 300 |
| cctcacgcct cgaacacga ccactcgttc tcgcgtaagg actacaagca gggcgttgcg | 360 |
| aactcgaacg acttcatcga caaccgtaac ttcgacgccg aaaccttcca gacttccctt | 420 |
| gacgtggttg ccggtaagac gcacttcgat tacgccgaca tgaacgagat tcgcctgcag | 480 |
| cgcgaatcgc ttagcaacga gctggacttc ccgggttggt tcaccgaatc caagccgatc | 540 |
| cagaacgttg aatccggctt tatcttcgcc ctggtgagcg acttcaacct gccggataac | 600 |
| gacgaaaacc cgctggttcg catcgactgg tggaagtact ggttcaccaa cgaatccttc | 660 |
| ccgtaccacc tgggctggca cccaccgtcc ccggcccgcg aaatcgaatt cgtcacctcc | 720 |
| gccagctcgg cggttctcgc ggcatcggtt acctcgaccc cgtcctcgct gccgtcgggc | 780 |
| gccatcggcc cgggcgcaga ggctgttccg ctgtcgttcg cgtcgaccat gaccccgttc | 840 |
| ctgctggcta ccaacgctcc gtactacgct caggacccaa ccctgcgccc gcagcgccag | 900 |
| gcccaccacc accaccacca ctga | 924 |

<210> SEQ ID NO 5
<211> LENGTH: 1007
<212> TYPE: DNA
<213> ORGANISM: Artificial Sequence
<220> FEATURE:
<223> OTHER INFORMATION: UPO gene

<400> SEQUENCE: 5

| | |
|---|---|
| atggaaccgg gtctgccccc gggtccgctg agaactcct ccgcgaagct ggtaaacgac | 60 |
| gaggcgcacc cttggaagcc gctccgccca ggcgacatcc gcggtccgtg cccgggtctg | 120 |
| aacaccctgg cgagccacgg ctacctgccg cgcaacggtg tcgccacccc agtccagatc | 180 |
| atcaatgccg tccaggaagg tctgaacttc gacaaccagg ctgccgtctt cgcgacctac | 240 |
| gccgcccacc tggttgacgg caacctgatc actgacctgc tgtcgatcgg tcgtaagacc | 300 |
| cgcctgaccg gccggaccc accgccccg gcgtcggttg gcggtctgaa cgagcacggc | 360 |
| accttcgaag gcgacgcctc catgacccgc ggtgacgcct ttttcggtaa caaccacgac | 420 |
| ttcaacgaga ccctgttcga gcagctggtc gactattcca accgtttcgg tggcggcaag | 480 |
| tacaacctga ccgtggccgg cgaactgcgc ttcaagcgta tccaggactc gatcgccacc | 540 |
| aacccgaact ctcccttcgt tgacttccgc ttcttcaccg cctacggcga gaccaccttc | 600 |
| ccagccaacc tgttcgttga cggccgccgt gacgacggtc agctggatat ggacgccgca | 660 |
| cgttcgttct tccagttcag ccgcatgccg gacgacttct ccgcgcccc gtcgccgcgt | 720 |
| tccggcaccg tgttgaggt tgtcatccag gcccacccga tgcagccggg ccgcaacgtc | 780 |
| ggcaagatca actcctacac cgtggaccct acctcgagcg acttcagcac cccgtgcctg | 840 |
| atgtacgaaa aattcgtcaa tatcaccgtg aaaagcctgt acccgaaccc gaccgttcag | 900 |
| ctgcgtaagg ccctgaacac caatctggat ttcttcttcc agggtgtcgc agccggttgc | 960 |
| acgcaggttt tcccttacgg ccgcgaccac caccaccacc accacta | 1007 |

<210> SEQ ID NO 6
<211> LENGTH: 1647

```
<212> TYPE: DNA
<213> ORGANISM: Artificial Sequence
<220> FEATURE:
<223> OTHER INFORMATION: PAMO gene

<400> SEQUENCE: 6
atggcaggcc agactaccgt agattcgcgc cgccaacctc cggaagaagt cgacgttctg      60
gtcgtgggcg ccggtttcag cggtctgtac gccctctacc gtctgcgtga gctgggtcgt     120
agcgttcacg ttatcgagac cgcaggcgac gtcggtggtg tctggtactg gaaccgctac     180
cctggtgccc gttgcgacat cgaaagcatc gagtactgct acagcttcag cgaagaagta     240
ctgcaggagt ggaattggac cgagcgttac gcttcccagc cggaaatcct ccgctacatc     300
aacttcgtgg cagataagtt cgatctgcgc agcggcatca ccttccacac cactgttacg     360
gcggccgctt tcgacgaagc gactaacact tggaccgtgg acaccaacca cggcgaccgt     420
attcgcgccc gttacctgat catggccagc ggtcagctct cggtacctca gctgcctaac     480
ttccctggcc tgaaggattt cgcgggcaac ctgtaccaca ccggcaactg gccgcacgag     540
ccagtagatt tctccggcca gcgtgttggc gtcatcggca ccggttcgtc gggcatccag     600
gtctccccgc agatcgccaa gcaagcggca gagctgttcg tgttccagcg caccccgcac     660
ttcgctgtcc cggcccgcaa cgcaccgctc gacccggaat tcctggccga cctgaagaag     720
cgttacgccg agttccgtga agaatcgcgc aacacccctg cggcaccca ccgctaccag     780 ggcccgaaga gcgctctgga agtgtccgac gaagaactgg tggaaaccct ggagcgttac     840
tggcaagagg gcggcccgga catcctcgcc gcctaccgtg acatcctgcg cgaccgtgac     900
gccaacgaac gtgtcgccga gttcatccgt aacaaaatcc gtaacaccgt gcgtgacccg     960
gaagttgccg agcgtctggt cccgaaaggc tacccgttcg gcaccaagcg cctgatcctc    1020
gagatcgact actacgaaat gttcaaccgc gataacgttc acctggttga caccctgagc    1080
gctccgatcg agaccatcac ccccgtggt gtccgtactt cggaacgtga gtacgaactg    1140
gattccctgg ttctggctac cggcttcgac gccctgaccg tgccctgtt caagatcgac    1200 atccgcggtg tgggtaacgt tgcactgaag gagaagtggg ctgctggccc gcgtacttac    1260
ctgggcctgt cgaccgccgg cttcccgaac ctgttcttca tcgccgggcc gggcagcccg    1320
agcgccctgt cgaacggcct ggtttccatc gagcagcacg tcgaatgggt gactgaccac    1380
atcgcttaca tgttcaaaaa tggtctgacc cgctcggaag ccgttctgga aggaagat    1440 gagtgggtgg aacacgttaa cgaaatcgcc gacgaaaccc tgtaccctat gaccgcttcg    1500
tggtacactg gcgctaacgt cccaggtaag ccacgcgtct tcatgctgta cgttggcggc    1560
ttccaccgct accgccagat ctgcgacgag gtggctgcaa agggctatga gggtttcgtg    1620
ctgacccacc accaccacca ccactga                                        1647

<210> SEQ ID NO 7
<211> LENGTH: 1941
<212> TYPE: DNA
<213> ORGANISM: Artificial Sequence
<220> FEATURE:
<223> OTHER INFORMATION: GOase gene

<400> SEQUENCE: 7
atggcttccg ccccgatcgg ttccgccatt ccacgcaaca actgggctgt cacgtgcgac      60
tccgctcagt ctggtaacga gtgcaacaag gccatcgacg caacaagga cccttctgg     120 cacacctttt acggcgccaa cggtgacccg aaaccacctc acacctatac catcgacatg     180
```

| | |
|---|---|
| aagaccactc agaacgtgaa cggcctgtcc gttctgcctc gtcaggacgg taaccagaac | 240 |
| ggttggatcg gtcgtcacga agtgtacctg tcgtcggacg gcaccaactg gggctccccg | 300 |
| gtggcttcgg gctcctggtt cgccgactcg accaccaagt actccaactt cgaaacccgt | 360 |
| ccggcccgtt acgtgcgtct ggttgcagtc accgaagcca acggccagcc gtggacctcc | 420 |
| atcgccgaga tcaacgttt ccaggcctct tcctacaccg ccccacagcc tggcctgggc | 480 |
| cgttggggcc cgaccatcga ccttccgatc gtcccagcgg ctgccgccat cgagccgacc | 540 |
| agcggtcgcg ttctgatgtg agcagctac cgcaacgacg ctttcgaggg cagcccgggc | 600 |
| ggtattactc tcacctcgag ctgggacccg tccactggca tcgttagcga tcgtaccgtg | 660 |
| accgtcacta agcacgacat gttctgccca ggtatctcca tggacggcaa cggtcagatc | 720 |
| gtggttaccg gcggtaacga cgctaagaaa actagcctgt acgactcgtc gtccgactcg | 780 |
| tggatcccgg gcccggacat gcaggtcgct cgtggttacc agagctccgc caccatgtcc | 840 |
| gacggccgtg tcttcactat tggtggttcc ttctcgggcg gcgttttcga gaaaaacggt | 900 |
| gaagtatact ccccgtcctc gaagacctgg acgtccctgc caaacgcgaa ggtaaacccg | 960 |
| atgctgactg ccgacaaaca gggcctgtac atgtcggaca ccacgcctg gctgttcggc | 1020 |
| tggaaaaagg gctcggtctt ccaggctggt ccaagcaccg ccatgaactg gtactacacc | 1080 |
| tccggctccg gcgacgtgaa atcggctggt aaacgtcaga gcaaccgcgg tgtggcccca | 1140 |
| gatgcgatgt gcgtaacgc cgtcatgtac gacgctgtga agggcaaaat tctgaccttc | 1200 |
| ggtggctccc cggactacac cgactcggat gccaccacta acgcccacat catcaccctg | 1260 |
| ggtgaaccgg gtacctcgcc aaacaccgtg ttcgccagca acggtctgta cttcgcccgt | 1320 |
| acattccaca cttccgtggt cctgccggat ggtagcactt ttatcaccgg cggtcagcgt | 1380 |
| cgtggcatcc cgttcgagga ctccaccccg gtcttcactc cggagatcta cgttcctgaa | 1440 |
| caggacacct tctacaagca gaacccgaac agcatcgttc gcgcatacca cagcatctcc | 1500 |
| ctgctgcttc cggatggccg cgtcttcaac ggcggtggtg gcctgtgcgg cgactgcacc | 1560 |
| accaaccact cgacgctca gatcttcacc ccgaactacc tgtacgactc caacggcaac | 1620 |
| ctggctaccc gtccgaagat caccccgtacc agtactcagt ccgttaaagt cggcggtcgt | 1680 |
| atcaccattt cgactgactc ctcgatcacc aaggcctcct tgatccgcta cggtaccgcg | 1740 |
| acccacacgg taaataccga ccagcgtcgc atcccgctga ccctgaccaa caacggtggc | 1800 |
| aacagctact ccttccaggt tccgagcgac tcgggtgtcg ccctgccggg ctactggatg | 1860 |
| ctgttcgtca tgaactcggc cggcgtaccg tccgtggcca gcactatccg cgtcacgcag | 1920 |
| caccaccacc accaccactg a | 1941 |

<210> SEQ ID NO 8
<211> LENGTH: 3160
<212> TYPE: DNA
<213> ORGANISM: Artificial Sequence
<220> FEATURE:
<223> OTHER INFORMATION: RSF1010 ori

<400> SEQUENCE: 8

| | |
|---|---|
| atgaagaacg acaggacttt gcaggccata ggccgacagc tcaaggccat gggctgtgag | 60 |
| cgcttcgata tcggcgtcag ggacgcaccc accggccaga tgatgaaccg ggaatggtca | 120 |
| gccgccgaag tgctccagaa cacgccatgg ctcaagcgga tgaatgccca ggcaatgac | 180 |
| gtgtatatca ggcccgccga gcaggagcgg catggtctgg tgctggtgga cgacctcagc | 240 |
| gagtttgacc tggatgacat gaaagccgag ggccgggagc ctgccctggt agtggaaacc | 300 |

```
agcccgaaga actatcaggc atgggtcaag gtggccgacg ccgcaggcgg tgaacttcgg     360
gggcagattg cccggacgct ggccagcgag tacgacgccg acccgccag cgccgacagc     420 cgccactatg ccgcttggc gggcttcacc aaccgcaagg acaagcacac cacccgcgcc     480
ggttatcagc cgtgggtgct gctgcgtgaa tccaagggca agaccgccac cgctggcccg     540
gcgctggtgc agcaggctgg ccagcagatc gagcaggccc agcggcagca ggagaaggcc     600
cgcaggctgg ccagcctcga actgcccgag cggcagctta gccgccaccg cgcacggcg     660 ctggacgagt accgcagcga gatggccggg ctggtcaagc gcttcggtca tgacctcagc     720
aagtgcgact ttatcgccgc gcagaagctg ccagccgggg ccgcagtgc cgaggaaatc     780 ggcaaggcca tggccgaggc cagcccagcg ctggcagagc gcaagcccgg ccacgaagcg     840
gattacatcg agcgcaccgt cagcaaggtc atgggtctgc ccagcgtcca gcttgcgcgg     900
gccgagctgg cacgggcacc ggcaccccgc cagcgaggca tggacagggg cgggccagat     960
ttcagcatgt agtgcttgcg ttggtactca cgcctgttat actatgagta ctcacgcaca    1020 gaaggggggtt ttatggaata cgaaaaaagc gcttcagggt cggtctacct gatcaaaagt    1080 gacaaggggct attggttgcc cggtggcttt ggttatacgt caaacaaggc cgaggctggc    1140
cgcttttcag tcgctgatat ggccagcctt aaccttgacg gctgcacctt gtccttgttc    1200
cgcgaagaca agcctttcgg ccccggcaag tttctcggtg actgatatga agaccaaaa    1260 ggacaagcag accggcgacc tgctggccag ccctgacgct gtacgccaag cgcgatatgc    1320
cgagcgcatg aaggccaaag ggatgcgtca gcgcaagttc tggctgaccg acgacgaata    1380
cgaggcgctg cgcgagtgcc tggaagaact cagagcggcg cagggcgggg gtagtgaccc    1440
cgccagcgcc taaccaccaa ctgcctgcaa aggaggcaat caatggctac ccataagcct    1500
atcaatattc tggaggcgtt cgcagcagcg ccgccaccgc tggactacgt tttgcccaac    1560
atggtggccg gtacggtcgg ggcgctggtg tcgcccggtg gtgccggtaa atccatgctg    1620
gccctgcaac tggccgcaca gattgcaggc gggccggatc tgctggaggt gggcgaactg    1680
cccaccggcc cggtgatcta cctgcccgcc gaagacccgc ccaccgccat tcatcaccgc    1740
ctgcacgccc ttggggcgca cctcagcgcc gaggaacggc aagccgtggc tgacggcctg    1800
ctgatccagc cgctgatcgg cagcctgccc aacatcatgg ccccggagtg gttcgacggc    1860
ctcaagcgcg ccgccgaggg ccgccgcctg atggtgctgg acacgctgcg ccggttccac    1920
atcgaggaag aaaacgccag cggccccatg gcccaggtca tcggtcgcat ggaggccatc    1980
gccgccgata ccgggtgctc tatcgtgttc ctgcaccatg ccagcaaggg cgcggccatg    2040
atgggcgcag cgaccagca gcaggccagc cggggcagct cggtactggt cgataacatc    2100
cgctggcagt cctacctgtc gagcatgacc agcgccgagg ccgaggaatg gggtgtggac    2160
gacgaccagc gccggttctt cgtccgcttc ggtgtgagca aggccaacta tggcgcaccg    2220
ttcgctgatc ggtggttcag gcggcatgac ggcggggtgc tcaagcccgc cgtgctggag    2280
aggcagcgca agagcaaggg ggtgccccgt ggtgaagcct aagaacaagc acagcctcag    2340
ccacgtccgg cacgacccgg cgcactgtct ggccccccggc ctgttccgtg ccctcaagcg    2400
gggcgagcgc aagcgcagca agctggacgt gacgtatgac tacggcgacg gcaagcggat    2460
cgagttcagc ggcccggagc cgctgggcgc tgatgatctg cgcatcctgc aagggctggt    2520
ggccatggct gggcctaatg gcctagtgct tggcccggaa cccaagaccg aaggcggacg    2580
gcagctccgg ctgttcctgg aacccaagtg ggaggccgtc accgctgaat gccatgtggt    2640
```

| | |
|---|---|
| caaaggtagc tatcgggcgc tggcaaagga atcggggca gaggtcgata gtggtgggc | 2700 |
| gctcaagcac atacaggact gcatcgagcg cctttggaag gtatccatca tcgcccagaa | 2760 |
| tggccgcaag cggcagggt ttcggctgct gtcggagtac gccagcgacg aggcggacgg | 2820 |
| gcgcctgtac gtggccctga acccttgat cgcgcaggcc gtcatgggtg gcggccagca | 2880 |
| tgtgcgcatc agcatggacg aggtgcgggc gctggacagc gaaaccgccc gcctgctgca | 2940 |
| ccagcggctg tgtggctgga tcgaccccgg caaaaccggc aaggcttcca tagatacctt | 3000 |
| gtgcggctat gtctggccgt cagaggccag tggttcgacc atgcgcaagc gccgcaagcg | 3060 |
| ggtgcgcgag gcgttgccgg agctggtcgc gctgggctgg acggtaaccg agttcgcggc | 3120 |
| gggcaagtac gacatcaccc ggcccaaggc ggcaggctga | 3160 |

<210> SEQ ID NO 9
<211> LENGTH: 534
<212> TYPE: DNA
<213> ORGANISM: Artificial Sequence
<220> FEATURE:
<223> OTHER INFORMATION: GmR

<400> SEQUENCE: 9

| | |
|---|---|
| ttaggtggcg gtacttgggt cgatatcaaa gtgcatcact tcttcccgta tgcccaactt | 60 |
| tgtatagaga gccactgcgg gatcgtcacc gtaatctgct tgcacgtaga tcacataagc | 120 |
| accaagcgcg ttggcctcat gcttgaggag attgatgagc gcggtggcaa tgccctgcct | 180 |
| ccggtgctcg ccggagactg cgagatcata gatatagatc tcactacgcg gctgctcaaa | 240 |
| cctgggcaga acgtaagccg cgagagcgcc aacaaccgct tcttggtcga aggcagcaag | 300 |
| cgcgatgaat gtcttactac ggagcaagtt cccgaggtaa tcggagtccg gctgatgttg | 360 |
| ggagtaggtg gctacgtctc cgaactcacg accgaaaaga tcaagagcag cccgcatgga | 420 |
| tttgacttgg tcagggccga gcctacatgt gcgaatgatg cccatacttg agccacctaa | 480 |
| cttttgtttta gggcgactgc cctgctgcgt aacatcgttg ctgctgcgta acat | 534 |

<210> SEQ ID NO 10
<211> LENGTH: 879
<212> TYPE: DNA
<213> ORGANISM: Artificial Sequence
<220> FEATURE:
<223> OTHER INFORMATION: araC gene

<400> SEQUENCE: 10

| | |
|---|---|
| atggctgaag cgcaaaatga tccccctgctg ccgggatact cgtttaatgc ccatctggtg | 60 |
| gcgggtttaa cgccgattga ggccaacggt tatctcgatt ttttttatcga ccgaccgctg | 120 |
| ggaatgaaag gttatattct caatctcacc attcgcggtc aggggggtggt gaaaaatcag | 180 |
| ggacgagaat ttgtttgccg accgggtgat attttgctgt tcccgccagg agagattcat | 240 |
| cactacggtc gtcatccgga ggctcgcgaa tggtatcacc agtgggttta ctttcgtccg | 300 |
| cgcgcctact ggcatgaatg gcttaactgg ccgtcaatat ttgccaatac ggggttcttt | 360 |
| cgcccggatg aagcgcacca gccgcatttc agcgacctgt ttgggcaaat cattaacgcc | 420 |
| gggcaagggg aagggcgcta ttcggagctg ctggcgataa atctgcttga gcaattgtta | 480 |
| ctgcggcgca tggaagcgat taacgagtcg ctccatccac cgatggataa tcgggtacgc | 540 |
| gaggcttgtc agtacatcag cgatcacctg gcagacagca attttgatat cgccagcgtc | 600 |
| gcacagcatg tttgcttgtc gccgtcgcgt ctgtcacatc ttttccgcca gcagttaggg | 660 |
| attagcgtct taagctggcg cgaggaccaa cgtatcagcc aggcgaagct gctttttgagc | 720 |

```
accacccgga tgcctatcgc caccgtcggt cgcaatgttg gttttgacga tcaactctat      780
ttctcgcggg tatttaaaaa atgcaccggg gccagcccga gcgagttccg tgccggttgt      840
gaagaaaaag tgaatgatgt agccgtcaag ttgtcataa                             879
```

<210> SEQ ID NO 11
<211> LENGTH: 28
<212> TYPE: DNA
<213> ORGANISM: Artificial Sequence
<220> FEATURE:
<223> OTHER INFORMATION: araBAD promoter

<400> SEQUENCE: 11

```
gacgcttttt atcgcaactc tctactgt                                         28
```

<210> SEQ ID NO 12
<211> LENGTH: 417
<212> TYPE: DNA
<213> ORGANISM: Artificial Sequence
<220> FEATURE:
<223> OTHER INFORMATION: Gam gene

<400> SEQUENCE: 12

```
atggatatta atactgaaac tgagatcaag caaaagcatt cactaacccc ctttcctgtt      60
ttcctaatca gcccggcatt tcgcgggcga tattttcaca gctatttcag gagttcagcc      120
atgaacgctt attacattca ggatcgtctt gaggctcaga gctgggcgcg tcactaccag      180
cagctcgccc gtgaagagaa agaggcagaa ctggcagacg acatggaaaa aggcctgccc      240
cagcacctgt ttgaatcgct atgcatcgat catttgcaac gccacggggc cagcaaaaaa      300
tccattaccc gtgcgtttga tgacgatgtt gagtttcagg agcgcatggc agaacacatc      360
cggtacatgg ttgaaaccat tgctcaccac caggttgata ttgattcaga ggtataa        417
```

<210> SEQ ID NO 13
<211> LENGTH: 786
<212> TYPE: DNA
<213> ORGANISM: Artificial Sequence
<220> FEATURE:
<223> OTHER INFORMATION: Bet gene

<400> SEQUENCE: 13

```
atgagtactg cactcgcaac gctggctggg aagctggctg aacgtgtcgg catggattct      60
gtcgacccac aggaactgat caccactctt cgccagacgg catttaaagg tgatgccagc      120
gatgcgcagt tcatcgcatt actgatcgtt gccaaccagt acggccttaa tccgtggacg      180
aaagaaattt acgcctttcc tgataagcag aatggcatcg ttccggtggt gggcgttgat      240
ggctggtccc gcatcatcaa tgaaaaccag cagtttgatg catggacttt gagcaggac       300 aatgaatcct gtacatgccg gatttaccgc aaggaccgta atcatccgat ctgcgttacc      360
gaatggatgg atgaatgccg ccgcgaacca ttcaaaactc gcgaaggcag agaaatcacg      420
gggccgtggc agtcgcatcc caaacggatg ttacgtcata aagccatgat tcagtgtgcc      480
cgtctggcct tcggatttgc tggtatctat gacaaggatg aagccgagcg cattgtcgaa      540
aatactgcat acactgcaga acgtcagccg gaacgcgaca tcactccggt taacgatgaa      600
accatgcagg agattaacac tctgctgatc gccctggata aacatgggga tgacgactta     660
ttgccgctct gttcccagat atttcgccgc gacattcgtg catcgtcaga actgacacag     720
gccgaagcag taaaagctct tggattcctg aaacagaaag ccgcagagca gaaggtggca     780
``` gcatga                                                                786

<210> SEQ ID NO 14
<211> LENGTH: 681
<212> TYPE: DNA
<213> ORGANISM: Artificial Sequence
<220> FEATURE:
<223> OTHER INFORMATION: Exo gene

<400> SEQUENCE: 14
atgacaccgg acattatcct gcagcgtacc gggatcgatg tgagagctgt cgaacagggg    60
gatgatgcgt ggcacaaatt acggctcggc gtcatcaccg cttcagaagt tcacaacgtg   120
atagcaaaac cccgctccgg aaagaagtgg cctgacatga aaatgtccta cttccacacc   180
ctgcttgctg aggtttgcac cggtgtggct ccggaagtta acgctaaagc actggcctgg   240
ggaaaacagt acgagaacga cgccagaacc ctgtttgaat tcacttccgg cgtgaatgtt   300
actgaatccc cgatcatcta tcgcgacgaa agtatgcgta ccgcctgctc tcccgatggt   360
ttatgcagtg acgcaacgg ccttgaactg aaatgcccgt ttacctcccg ggatttcatg   420
aagttccggc tcggtggttt cgaggccata agtcagctt acatggccca ggtgcagtac   480
agcatgtggg tgacgcgaaa aaatgcctgg tactttgcca actatgaccc gcgtatgaag   540
cgtgaaggcc tgcattatgt cgtgattgag cgggatgaaa agtacatggc gagttttgac   600
gagatcgtgc cggagttcat cgaaaaaatg gacgaggcac tggctgaaat tggttttgta   660
tttggggagc aatggcgatg a                                             681

<210> SEQ ID NO 15
<211> LENGTH: 73
<212> TYPE: DNA
<213> ORGANISM: Artificial Sequence
<220> FEATURE:
<223> OTHER INFORMATION: Tet promoter

<400> SEQUENCE: 15
taattcctaa ttttttgttga cactctatcg ttgatagagt tattttacca ctccctatca    60
gtgatagaga aaa                                                       73

<210> SEQ ID NO 16
<211> LENGTH: 4107
<212> TYPE: DNA
<213> ORGANISM: Artificial Sequence
<220> FEATURE:
<223> OTHER INFORMATION: SpCas9 gene

<400> SEQUENCE: 16
atggataaga aatactcaat aggcttagat atcggcacaa atagcgtcgg atgggcggtg    60
atcactgatg aatataaggt tccgtctaaa aagttcaagg ttctgggaaa tacagaccgc   120
cacagtatca aaaaaatct atagggggct cttttatttg acagtggaga cagcggaa    180
gcgactcgtc tcaaacggac agctcgtaga aggtatacac gtcggaagaa tcgtatttgt   240
tatctacagg agatttttc aaatgagatg gcgaaagtag atgatagttt ctttcatcga   300
cttgaagagt cttttttggt ggaagaagac aagaagcatg aacgtcatcc tattttttgga   360
aatatagtag atgaagttgc ttatcatgag aaatatccaa ctatctatca tctgcgaaaa   420
aaattggtag attctactga taaagcggat ttgcgcttaa tctatttggc cttagcgcat   480
atgattaagt ttcgtggtca ttttttgatt gagggagatt taaatcctga taatagtgat   540
gtggacaaac tatttatcca gttggtacaa acctacaatc aattatttga agaaaaccct   600

```
attaacgcaa gtggagtaga tgctaaagcg attctttctg cacgattgag taaatcaaga    660
cgattagaaa atctcattgc tcagctcccc ggtgagaaga aaaatggctt atttgggaat    720
ctcattgctt tgtcattggg tttgacccct aatttttaaat caaattttga tttggcagaa   780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taagaaaatc tttttttgatc aatcaaaaaa cggatatgca   1080
ggttatattg atgggggagc tagccaagaa gaatttata aatttatcaa accaattttta   1140 gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga gaagcaaga agacttttat ccattttaa aagacaatcg tgagaagatt    1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aggtgcttc agctcaatca tttattgaac gcatgacaaa ctttgataaa    1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaagaaga ttatttcaaa aaaatagaat gttttgatag tgttgaaatt    1740
tcaggagttg aagatagatt taatgcttca ttaggtacct accatgattt gctaaaaatt   1800 attaagata aagatttttt ggataatgaa gaaaatgaag atatcttaga ggatatttgt    1860
ttaacattga cctttattga agataggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gattttttga atcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaggtat tttacagact   2220 gtaaagttg ttgatgaatt ggtcaaagta atggggcggc ataagccaga aaatatcgtt    2280
attgaaatgg cacgtgaaaa tcagacaact caaaagggcc agaaaaattc gcgagagcgt   2340
atgaaacgaa tcgaagaagg tatcaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taagacgat tcaatagaca ataaggtctt aacgcgttct    2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
aaattagttt ctgacttccg aaaagatttc caattctata agtacgtga gattaacaat   2940
```

| | |
|---|---|
| taccatcatg cccatgatgc gtatctaaat gccgtcgttg gaactgcttt gattaagaaa | 3000 |
| tatccaaaac ttgaatcgga gtttgtctat ggtgattata agtttatga tgttcgtaaa | 3060 |
| atgattgcta agtctgagca agaaataggc aaagcaaccg caaatatttt cttttactct | 3120 |
| aatatcatga acttcttcaa aacagaaatt acacttgcaa atggagagat tcgcaaacgc | 3180 |
| cctctaatcg aaactaatgg ggaaactgga gaattgtct gggataaagg gcgagatttt | 3240 |
| gccacagtgc gcaaagtatt gtccatgccc caagtcaata ttgtcaagaa aacagaagta | 3300 |
| cagacaggcg gattctccaa ggagtcaatt ttaccaaaaa gaaattcgga caagcttatt | 3360 |
| gctcgtaaaa aagactggga tccaaaaaaa tatggtggtt ttgatagtcc aacggtagct | 3420 |
| tattcagtcc tagtggttgc taaggtggaa aaagggaaat cgaagaagtt aaaatccgtt | 3480 |
| aaagagttac tagggatcac aattatgaaa agaagttcct ttgaaaaaaa tccgattgac | 3540 |
| tttttagaag ctaaaggata taggaagtt aaaaaagact taatcattaa actacctaaa | 3600 |
| tatagtcttt ttgagttaga aaacggtcgt aaacggatgc tggctagtgc cggagaatta | 3660 |
| caaaaaggaa atgagctggc tctgccaagc aaatatgtga atttttata tttagctagt | 3720 |
| cattatgaaa agttgaaggg tagtccagaa gataacgaac aaaaacaatt gtttgtggag | 3780 |
| cagcataagc attatttaga tgagattatt gagcaaatca gtgaattttc taagcgtgtt | 3840 |
| attttagcag atgccaattt agataaagtt cttagtgcat ataacaaaca tagagacaaa | 3900 |
| ccaatacgtg aacaagcaga aaatattatt cattattta cgttgacgaa tcttggagct | 3960 |
| cccgctgctt ttaaatattt tgatacaaca attgatcgta acgatatac gtctacaaaa | 4020 |
| gaagttttag atgccactct tatccatcaa tccatcactg gtctttatga aacacgcatt | 4080 |
| gatttgagtc agctaggagg tgactga | 4107 |

<210> SEQ ID NO 17
<211> LENGTH: 3156
<212> TYPE: DNA
<213> ORGANISM: Artificial Sequence
<220> FEATURE:
<223> OTHER INFORMATION: SaCas9 gene

<400> SEQUENCE: 17

| | |
|---|---|
| atgaagcgga actacatcct gggcctggac atcggcatca ccagcgtggg ctacggcatc | 60 |
| atcgactacg agacacggga cgtgatcgat gccggcgtgc ggctgttcaa agaggccaac | 120 |
| gtggaaaaca cgagggcag gcggagcaag agaggcgcca aaggctgaa gcggcggagg | 180 |
| cggcatagaa tccagagagt gaagaagctg ctgttcgact acaacctgct gaccgaccac | 240 |
| agcgagctga gcggcatcaa ccctacgag gccagagtga agggcctgag ccagaagctg | 300 |
| agcgaggaag agttctctgc cgccctgctg cacctggcca agagaagagg cgtgcacaac | 360 |
| gtgaacgagg tggaagagga caccggcaac gagctgtcca ccaaagagca gatcagccgg | 420 |
| aacagcaagg ccctggaaga aaatacgtg gccgaactgc agctggaacg gctgaagaaa | 480 |
| gacggcgaag tgcggggcag catcaacaga ttcaagacca cgactacgt gaagaagcc | 540 |
| aaacagctgc tgaaggtgca gaaggcctac caccagctgg accagagctt catcgacacc | 600 |
| tacatcgacc tgctggaaac ccggcggacc tactatgagg acctggcga gggcagcccc | 660 |
| ttcggctgga aggacatcaa agaatggtac gagatgctga tgggccactg cacctacttc | 720 |
| cccgaggaac tgcggagcgt gaagtacgcc tacaacgccg acctgtacaa cgccctgaac | 780 |
| gacctgaaca atctcgtgat caccagggac gagaacgaga gctggaata ttacgagaag | 840 |
| ttccagatca tcgagaacgt gttcaagcag aagaagaagc ccaccctgaa gcagatcgcc | 900 |

```
aaagaaatcc tcgtgaacga agaggatatt aagggctaca gagtgaccag caccggcaag    960
cccgagttca ccaacctgaa ggtgtaccac gacatcaagg acattaccgc ccggaaagag   1020
attattgaga acgccgagct gctggatcag attgccaaga tcctgaccat ctaccagagc   1080
agcgaggaca tccaggaaga actgaccaat ctgaactccg agctgaccca ggaagagatc   1140
gagcagatct ctaatctgaa gggctatacc ggcacccaca acctgagcct gaaggccatc   1200
aacctgatcc tggacgagct gtggcacacc aacgacaacc agatcgctat cttcaaccgg   1260
ctgaagctgg tgcccaagaa ggtggacctg tcccagcaga agagatcccc caccaccctg   1320
gtggacgact tcatcctgag ccccgtcgtg aagagaagct tcatccagag catcaaagtg   1380
atcaacgcca tcatcaagaa gtacggcctg cccaacgaca tcattatcga gctggcccgc   1440
gagaagaact ccaaggacgc ccagaaaatg atcaacgaga tgcagaagcg gaaccggcag   1500
accaacgagc ggatcgagga aatcatccgg accaccggca agagaacgc caagtacctg   1560
atcgagaaga tcaagctgca cgacatgcag gaaggcaagt gcctgtacag cctggaagcc   1620
atccctctgg aagatctgct gaacaacccc ttcaactatg aggtggacca catcatcccc   1680
agaagcgtgt ccttcgacaa cagcttcaac aacaaggtgc tcgtgaagca ggaagaaaac   1740
agcaagaagg gcaaccggac cccattccag tacctgagca gcagcgacag caagatcagc   1800
tacgaaacct tcaagaagca catcctgaat ctggccaagg gcaagggcag aatcagcaag   1860
accaagaaag agtatctgct ggaagaacgg gacatcaaca ggttctccgt gcagaaagac   1920
ttcatcaacc ggaacctggt ggataccaga tacgccacca gaggcctgat gaacctgctg   1980
cggagctact tcagagtgaa caacctggac gtgaaagtga agtccatcaa tggcggcttc   2040
accagctttc tgcggcggaa gtggaagttt aagaaagagc ggaacaaggg gtacaagcac   2100
cacgccgagg acgccctgat cattgccaac gccgatttca tcttcaaaga gtggaagaaa   2160
ctggacaagg ccaaaaaagt gatggaaaac cagatgttcg aggaaaagca ggccgagagc   2220
atgcccgaga tcgaaaccga gcaggagtac aaagagatct tcatcacccc ccaccagatc   2280
aagcacatta aggacttcaa ggactacaag tacagccacc gggtggacaa gaagcctaat   2340
agagagctga ttaacgacac cctgtactcc acccggaagg acgacaaggg caacaccctg   2400
atcgtgaaca atctgaacgg cctgtacgac aaggacaatg acaagctgaa aaagctgatc   2460
aacaagagcc ccgaaaagct gctgatgtac caccacgacc cccagaccta ccagaaactg   2520
aagctgatta tggaacagta cggcgacgag aagaatcccc tgtacaagta ctacgaggaa   2580
accgggaact acctgaccaa gtactccaaa aaggacaacg gccccgtgat caagaagatt   2640
aagtattacg gcaacaaact gaacgcccat ctggacatca ccgacgacta ccccaacagc   2700
agaaacaagg tcgtgaagct gtccctgaag ccctacagat cgacgtgta cctggacaat   2760
ggcgtgtaca agttcgtgac cgtgaagaat ctggatgtga tcaaaaaaga aaactactac   2820
gaagtgaata gcaagtgcta tgaggaagct aagaagctga aagatcag caaccaggcc   2880
gagtttatcg cctccttcta caacaacgat ctgatcaaga tcaacggcga gctgtataga   2940
gtgatcggcg tgaacaacga cctgctgaac cggatcgaag tgaacatgat cgacatcacc   3000
taccgcgagt acctggaaaa catgaacgac aagaggcccc ccaggatcat aagacaatc   3060
gcctccaaga cccagagcat taagaagtac agcacagaca ttctgggcaa cctgtatgaa   3120
gtgaaatcta agaagcaccc tcagatcatc aaaaag                             3156
```

<210> SEQ ID NO 18

<211> LENGTH: 3903
<212> TYPE: DNA
<213> ORGANISM: Artificial Sequence
<220> FEATURE:
<223> OTHER INFORMATION: FnCas12a gene

<400> SEQUENCE: 18

| | |
|---|---|
| atgtcaattt atcaagaatt tgttaataaa tatagtttaa gtaaaactct aagatttgag | 60 |
| ttaatcccac agggtaaaac acttgaaaac ataaaagcaa gaggtttgat tttagatgat | 120 |
| gagaaaagag ctaaagacta caaaaaggct aaacaaataa ttgataaata tcatcagttt | 180 |
| tttatagagg agatattaag ttcggtttgt attagcgaag atttattaca aaactattct | 240 |
| gatgtttatt ttaaacttaa aaagagtgat gatgataatc tacaaaaaga tttttaaaagt | 300 |
| gcaaaagata cgataaagaa acaaatatct gaatatataa aggactcaga gaaatttaag | 360 |
| aatttgttta atcaaaaccct tatcgatgct aaaaaagggc aagagtcaga tttaattcta | 420 |
| tggctaaagc aatctaagga taatggtata gaactatttta aagccaatag tgatatcaca | 480 |
| gatatagatg aggcgttaga aataatcaaa tcttttaaag gttggacaac ttattttaag | 540 |
| ggttttcatg aaaatagaaa aaatgtttat agtagcaatg atattcctac atctattatt | 600 |
| tataggatag tagatgataa tttgcctaaa tttctagaaa ataaagctaa gtatgagagt | 660 |
| ttaaaagaca aagctccaga agctataaac tatgaacaaa ttaaaaaaga tttggcagaa | 720 |
| gagctaacct ttgatattga ctacaaaaca tctgaagtta tcaaagagt ttttttcactt | 780 |
| gatgaagttt ttgagatagc aaactttaat aattatctaa atcaaagtgg tattactaaa | 840 |
| tttaatacta ttattggtgg taaatttgta aatggtgaaa atacaaagag aaaaggtata | 900 |
| aatgaatata taaatctata ctcacagcaa ataaatgata aaacactcaa aaaatataaa | 960 |
| atgagtgttt tatttaagca aattttaagt gatacagaat ctaaatcttt tgtaattgat | 1020 |
| aagttagaag atgatagtga tgtagttaca acgatgcaaa gtttttatga gcaaatagca | 1080 |
| gcttttaaaa cagtagaaga aaaatctatt aagaaacac tatctttatt atttgatgat | 1140 |
| ttaaaagctc aaaaacttga tttgagtaaa atttatttta aaaatgataa atctcttact | 1200 |
| gatctatcac aacaagtttt tgatgattat agtgttattg gtacagcggt actagaatat | 1260 |
| ataactcaac aaatagcacc taaaaatctt gataacccta gtaagaaaga gcaagaatta | 1320 |
| atagccaaaa aaactgaaaa agcaaaatac ttatctctag aaactataaa gcttgcctta | 1380 |
| gaagaattta ataagcatag agatatagat aaacagtgta ggtttgaaga atacttgca | 1440 |
| aactttgcgg ctattccgat gatatttgat gaaatagctc aaaacaaaga caatttggca | 1500 |
| cagatatcta tcaaatatca aaatcaaggt aaaaaagacc tacttcaagc tagtgcggaa | 1560 |
| gatgatgtta agctatcaa ggatcttta gatcaaacta taatctctt acataaaacta | 1620 |
| aaaatatttc atattagtca gtcagaagat aaggcaaata ttttagacaa ggatgagcat | 1680 |
| ttttatctag tatttgagga gtgctacttt gagctagcga atatagtgcc tctttataac | 1740 |
| aaaattagaa actatataac tcaaaagcca tatagtgatg agaaatttaa gctcaatttt | 1800 |
| gagaactcga ctttggctaa tggttgggat aaaaataaag agcctgacaa tacggcaatt | 1860 |
| ttatttatca aagatgataa atattatctg ggtgtgatga ataagaaaaa taacaaaata | 1920 |
| tttgatgata aagctatcaa agaaaataaa ggcgagggtt ataaaaaaat tgtttataaa | 1980 |
| cttttacctg cgcaaataa aatgttacct aaggttttct tttctgctaa atctataaaa | 2040 |
| ttttataatc ctagtgaaga tatacttaga ataagaaatc attccacaca tacaaaaaat | 2100 |
| ggtagtcctc aaaaaggata tgaaaaattt gagtttaata ttgaagattg ccgaaaattt | 2160 |

```
atagatttt  ataaacagtc  tataagtaag  catccggagt  ggaaagattt  tggatttaga    2220
ttttctgata  ctcaaagata  taattctata  gatgaatttt  atagagaagt  tgaaaatcaa    2280
ggctacaaac  taactttga   aaatatatca  gagagctata  ttgatagcgt  agttaatcag    2340
ggtaaattgt  acctattcca  aatctataat  aaagatttt   cagcttatag  caaagggcga    2400
ccaaatctac  atactttata  ttggaaagcg  ctgtttgatg  agagaaatct  tcaagatgtg    2460
gtttataagc  taaatggtga  ggcagagctt  tttatcgta   aacaatcaat  acctaaaaaa    2520
atcactcacc  cagctaaaga  ggcaatagct  aataaaaaca  aagataatcc  taaaaaagag    2580
agtgtttttg  aatatgattt  aatcaaagat  aaacgcttta  ctgaagataa  gttttctctt    2640
cactgtccta  ttacaatcaa  ttttaaatct  agtggagcta  ataagttaa   tgatgaaatc    2700 aatttattgc  taaagaaaa   agcaaatgat  gttcatatat  taagtataga  tagaggtgaa    2760
agacatttag  cttactatac  ttggtagat   ggtaaaggca  atatcatcaa  acaagatact    2820
ttcaacatca  ttggtaatga  tagaatgaaa  acaaactacc  atgataagct  tgctgcaata    2880
gagaaagata  gggattcagc  taggaaagac  tggaaaaga   taaataacat  caaagagatg    2940
aaagagggct  atctatctca  ggtagttcat  gaaatagcta  agctagttat  agagtataat    3000
gctattgtgg  tttttgagga  tttaaatttt  ggatttaaaa  gagggcgttt  caaggtagag    3060
aagcaggtct  atcaaaagtt  agaaaaaatg  ctaattgaga  aactaaacta  tctagttttc    3120
aaagataatg  agtttgataa  aactggggga  gtgcttagag  cttatcagct  aacagcacct    3180
tttgagactt  ttaaaaagat  gggtaaacaa  acaggtatta  tctactatgt  accagctggt    3240
tttacttcaa  aaatttgtcc  tgtaactggt  tttgtaaatc  agttatatcc  taagtatgaa    3300
agtgtcagca  aatctcaaga  gttctttagt  aagtttgaca  agatttgtta  taaccttgat    3360
aagggctatt  ttgagtttag  ttttgattat  aaaaactttg  gtgacaaggc  tgccaaaggc    3420
aagtggacta  tagctagctt  tgggagtaga  ttgattaact  ttagaaattc  agataaaaat    3480
cataattggg  atactcgaga  agtttatcca  actaaagagt  tggagaaatt  gctaaaagat    3540
tattctatcg  aatatgggca  tggcgaatgt  atcaaagcag  ctatttgcgg  tgagagcgac    3600
aaaaagtttt  ttgctaagct  aactagtgtc  ctaaatacta  tcttacaaat  gcgtaactca    3660
aaaacaggta  ctgagttaga  ttatctaatt  tcaccagtag  cagatgtaaa  tggcaattc     3720 tttgattcgc  gacaggcgcc  aaaaaatatg  cctcaagatg  ctgatgccaa  tggtgcttat    3780
catattgggc  taaaaggtct  gatgctacta  ggtaggatca  aaaataatca  agagggcaaa    3840
aaactcaatt  tggttatcaa  aaatgaagag  tattttgagt  tcgtgcagaa  taggaataac    3900
taa                                                                        3903
```

<210> SEQ ID NO 19
<211> LENGTH: 589
<212> TYPE: DNA
<213> ORGANISM: Artificial Sequence
<220> FEATURE:
<223> OTHER INFORMATION: ColE1 ori

<400> SEQUENCE: 19

```
tttccatagg  ctccgccccc  ctgacgagca  tcacaaaaat  cgacgctcaa  gtcagaggtg     60
gcgaaacccg  acaggactat  aaagatacca  ggcgtttccc  cctggaagct  ccctcgtgcg    120
ctctcctgtt  ccgaccctgc  cgcttaccgg  atacctgtcc  gcctttctcc  cttcgggaag    180
cgtggcgctt  tctcaatgct  cacgctgtag  gtatctcagt  tcggtgtagg  tcgttcgctc    240
```

```
caagctgggc tgtgtgcacg aaccccccgt tcagcccgac cgctgcgcct tatccggtaa      300
ctatcgtctt gagtccaacc cggtaagaca cgacttatcg ccactggcag cagccactgg      360
taacaggatt agcagagcga ggtatgtagg cggtgctaca gagttcttga agtggtggcc      420
taactacggc tacactagaa ggacagtatt tggtatctgc gctctgctga agccagttac      480
cttcggaaaa agagttggta gctcttgatc cggcaaacaa accaccgctg gtagcggtgg      540 ttttttttgtt tgcaagcagc agattacgcg cagaaaaaaa ggatctcaa                589
```

```
<210> SEQ ID NO 20
<211> LENGTH: 1261
<212> TYPE: DNA
<213> ORGANISM: Artificial Sequence
<220> FEATURE:
<223> OTHER INFORMATION: HRL

<400> SEQUENCE: 20
agaatcaggt tcagggcaat agccacaatg gcgcacaggg cgatgccctt caggccccag       60
tcatccgggc cgtcaccgct gccgatcagc acgccgccga taccgaacac cagtgtcacc      120
gagacgatca ccaggttgcg tgcctcgccc aggtcaatct tgtggcggat catggtgttc      180
atgcccaccg ctgcaatcga gccgaacagc aggcaaagaa tgccgcccat caccggcacc      240
gggatgctct gcagcagcgc gccgaacttg ccgatgaacg caagggtaat ggcgaagacc      300
gccgcccagg tcatgatctt cgggttgtag ttcttggtca gcatcaccgc gccggtcact      360
tcggcatagg tggtgttggg cgggccgccg aacaggccgg ctgcagtagt cgccaggccg      420
tcgcccagca acgtccggtg caggccaggc ttttcaggt agtcacggcc ggtcacgctg      480
cccactgcaa tcaccccgcc gatatgctcg atcgccggcg ccagcgcaac cgggacgatg      540
aacagaatgg cctgccagtt gaacgcaggg gcggtgaaat tgggaatttc cagccacggt      600
gcggcagcga tcctggcggt gtcgaccacg ccaaaggcga acgacagggc aaagcccacc      660
agcacgccgg agatgatggg taccaggcgg aaaatgccct tgccgaatac ggcaacgatc      720
aaggttgtca gcagcgctgg catcgagatc agcatggccg tcttgtacgg catcagtgcc      780
gtaccgtccc cacctttgcc catcgccatg ttggcggcga tcggtgccat ggccaggccg      840
atggagatga tcaccgggcc gatcaccacc ggcggcagca tgcggtcgat gaaaccggtg      900
cctttgattt ttaccatcag ccccatgaag gtgtacacga agccggcagc cattacgcca      960
cccatggtct cggcaaggcc gaactggcct ttggcgagga tgatcggcgt gatgaaggca     1020
aagctcgagg ccaggaacac cggtacctga cgaccggtga ccagctggaa tagcagcgtg     1080
ccgatgccgg cggtgaacag cgcgacgttt gggtcgaggc cggtgatcag ggcatcagc      1140 accagcgcgc cgaatgccac gaagagcatc tgcgcgcccg aaacgacctg cgcgcagagc     1200
gggtcgttga agccgtcctg catggtcagg cgtccttttg cttggtgccg aagatcttgt     1260
c                                                                    1261
```

```
<210> SEQ ID NO 21
<211> LENGTH: 34
<212> TYPE: DNA
<213> ORGANISM: Artificial Sequence
<220> FEATURE:
<223> OTHER INFORMATION: Frt sequence

<400> SEQUENCE: 21
gaagttccta ttctctagaa agtataggaa cttc                                 34
```

<210> SEQ ID NO 22
<211> LENGTH: 1191
<212> TYPE: DNA
<213> ORGANISM: Artificial Sequence
<220> FEATURE:
<223> OTHER INFORMATION: TcR

<400> SEQUENCE: 22

```
atgaaatcta acaatgcgct catcgtcatc ctcggcaccg tcaccctgga tgctgtaggc      60
ataggcttgg ttatgccggt actgccgggc ctcttgcggg atatcgtcca ttccgacagc     120
atcgccagtc actatggcgt gctgctagcg ctatatgcgt tgatgcaatt tctatgcgca     180
cccgttctcg gagcactgtc cgaccgcttt ggccgccgcc cagtcctgct cgcttcgcta     240
cttggagcca ctatcgacta cgcgatcatg gcgaccacac ccgtcctgtg gatcctctac     300
gccgacgca tcgtggccgg catcaccggc gccacaggtg cggttgctgg cgcctatatc     360
gccgacatca ccgatgggga agatcgggct cgccacttcg ggctcatgag cgcttgtttc     420
ggcgtgggta tggtggcagg ccccgtggcc gggggactgt gggcgccat ctccttgcat     480
gcaccattcc ttgcggcggc ggtgctcaac ggcctcaacc tactactggg ctgcttccta     540
atgcaggagt cgcataaggg agagcgtcga ccgatgccct tgagagcctt caacccagtc     600
agctccttcc ggtgggcgcg gggcatgact atcgtcgccg cacttatgac tgtcttcttt     660
atcatgcaac tcgtaggaca ggtgccggca gcgctctggg tcattttcgg cgaggaccgc     720
tttcgctgga gcgcgacgat gatcggcctg tcgcttgcgg tattcggaat cttgcacgcc     780
ctcgctcaag ccttcgtcac tggtcccgcc accaaacgtt tcggcgagaa gcaggccatt     840
atcgccggca tggcggccga cgcgctgggc tacgtcttgc tggcgttcgc gacgcgaggc     900
tggatggcct tccccattat gattcttctc gcttccggcg gcatcgggat gcccgcgttg     960
caggccatgc tgtccaggca ggtagatgac gaccatcagg gacagcttca aggatcgctc    1020
gcggctctta ccagcctaac ttcgatcact ggaccgctga tcgtcacggc gatttatgcc    1080
gcctcggcga gcacatggaa cgggttggca tggattgtag gcgccgccct ataccttgtc    1140
tgcctccccg cgttgcgtcg cggtgcatgg agccgggcca cctcgacctg a             1191
```

<210> SEQ ID NO 23
<211> LENGTH: 214
<212> TYPE: DNA
<213> ORGANISM: Artificial Sequence
<220> FEATURE:
<223> OTHER INFORMATION: HCE promoter

<400> SEQUENCE: 23

```
acagattccc aatctcttgt taaataacga aaaggcatca atcaaaacgg cggcatgtct      60
ttctatattc cagcaatgtt ttataggga catattgatg aagatgggta tcaccttagt     120
aaaaaaagaa ttgctataag ctgctctttt ttgttcgtga tatactgata ataaattgaa     180
ttttcacact tctgaaaaaa ggagctggaa ccaa                                 214
```

<210> SEQ ID NO 24
<211> LENGTH: 939
<212> TYPE: DNA
<213> ORGANISM: Artificial Sequence
<220> FEATURE:
<223> OTHER INFORMATION: HRR

<400> SEQUENCE: 24

```
aaaaaaaccg cgctagatta atctattcag cctgtgctgt cgtctggtca ttctggacgt      60
```

```
tagtccataa atgcttgatc tgtgacgagc ggatgcgtac ctttgcccgc tttttccaaaa    120 tgccccccgg agcgcgccat gtccgccgat ctcgagcata tccgtcaagt catgcatgaa    180
gctgactgcc tgtacaccga agccgaagtc gaagcggcca tcgccaaagt cggcgagcag    240
atctgcaagg acctgcacga caagaacccg gttgtgttct gcgtgatgaa cggtggcctg    300
atcttctccg gcaaactgct gacccacctg cagttcccgc tggaagcctc gtacctgcat    360
gctacccgct accgcaacca gaccagcggt ggcgagcttt tctggaaggc caagccggaa    420
gtgtcgttca tcgaccgtga cgtgttgatc gttgacgata tcctcgacga aggccacacc    480
ctcagcgcca tcatcgagtt tgcaagcat gccggcgccc gctcggtgta caccgctgtg    540
ctgatcgaca aggaccacga ccgcaaggca agccctgacc tcaaggccaa ctatgtgggc    600
ctgccttgtg tcgatcgcta tatcttcggt tacggcatgg actacaaagg ttactggcgc    660
aacgctaacg gcatcttcgc cgtaaagggg ctgtaaccgt gcgccagcct gcgttcatcg    720
accaatcgct gttcgccggg ctggccgaaa aggccgctgc caacccgcgc gggcggcagc    780
accataactt tcacgctatg gaagagccct gccaccgcat ggccgtcggg ctgcaaccaa    840
gcacctacat tccgccgcat cgccatttga gcgccgacaa ggctgaaacc ttgatagcgc    900
tcaaggggcg ttttggcctg ttgatcttcg atgaacaag                            939

<210> SEQ ID NO 25
<211> LENGTH: 35
<212> TYPE: DNA
<213> ORGANISM: Artificial Sequence
<220> FEATURE:
<223> OTHER INFORMATION: J23119 promoter

<400> SEQUENCE: 25
ttgacagcta gctcagtcct aggtataata ctagt                                35

<210> SEQ ID NO 26
<211> LENGTH: 62
<212> TYPE: DNA
<213> ORGANISM: Artificial Sequence
<220> FEATURE:
<223> OTHER INFORMATION: sgRNA::UPP-Sp

<400> SEQUENCE: 26
ggatggcgga tctcacgagt gttttagagc tagaaatagc aagttaaaat aaggctagtc    60
cg                                                                   62

<210> SEQ ID NO 27
<211> LENGTH: 99
<212> TYPE: DNA
<213> ORGANISM: Artificial Sequence
<220> FEATURE:
<223> OTHER INFORMATION: sgRNA::UPP-Sa

<400> SEQUENCE: 27
ggcggtgtag atcttcacgt gttttagtac tctggaaaca gaatctacta aaacaaggca    60
aaatgccgtg tttatctcgt caacttgttg gcgagattt                            99

<210> SEQ ID NO 28
<211> LENGTH: 39
<212> TYPE: DNA
<213> ORGANISM: Artificial Sequence
<220> FEATURE:
<223> OTHER INFORMATION: CrRNA::UPP-Fn

<400> SEQUENCE: 28
```
aatttctact gttgtagatt ccaccacctc gatgccttc                                                39

<210> SEQ ID NO 29
<211> LENGTH: 20
<212> TYPE: DNA
<213> ORGANISM: Artificial Sequence
<220> FEATURE:
<223> OTHER INFORMATION: P1

<400> SEQUENCE: 29
gggtgttggc tgatatgtgt                                                                     20

<210> SEQ ID NO 30
<211> LENGTH: 20
<212> TYPE: DNA
<213> ORGANISM: Artificial Sequence
<220> FEATURE:
<223> OTHER INFORMATION: P2

<400> SEQUENCE: 30
cctatgccta cagcatccag                                                                     20

<210> SEQ ID NO 31
<211> LENGTH: 20
<212> TYPE: DNA
<213> ORGANISM: Artificial Sequence
<220> FEATURE:
<223> OTHER INFORMATION: P3

<400> SEQUENCE: 31
acgtcccagg catcaaataa                                                                     20

<210> SEQ ID NO 32
<211> LENGTH: 19
<212> TYPE: DNA
<213> ORGANISM: Artificial Sequence
<220> FEATURE:
<223> OTHER INFORMATION: P4

<400> SEQUENCE: 32
gaaggagcac tctagcacg                                                                      19

<210> SEQ ID NO 33
<211> LENGTH: 20
<212> TYPE: DNA
<213> ORGANISM: Artificial Sequence
<220> FEATURE:
<223> OTHER INFORMATION: P5

<400> SEQUENCE: 33 ttttccacc acctcgatgc                                                                      20

<210> SEQ ID NO 34
<211> LENGTH: 19
<212> TYPE: DNA
<213> ORGANISM: Artificial Sequence
<220> FEATURE:
<223> OTHER INFORMATION: P6

<400> SEQUENCE: 34 gaatttcgc gaactcgcc                                                                       19

<210> SEQ ID NO 35
<211> LENGTH: 1326
<212> TYPE: DNA

<213> ORGANISM: Artificial Sequence
<220> FEATURE:
<223> OTHER INFORMATION: HmfT1 gene

<400> SEQUENCE: 35

```
atggaggcgg tggccaagaa gcgcaccgaa accatcagcg aggccttgcc ggcggccacc    60
aatcgccaag tgttcggcgc cgtgacggcc agctgtatgg gctgggccct ggacttgttc   120
gatctgttca tcctgttgtt cgtcgccccg gtgatcggcc gtctgttctt cccgtcggag   180
cacgccatgc tgagcttggc cgccgtgtac gccagcttcg cggtgacctt gctgatgcgc   240
ccgttgggca gcgccatctt tggcacctac gccgatcgtc atggtcgtaa gggcgctatg   300
gttgtggcgg tgaccggtgt cggcttgtcg accgccgcct tcggtctgct gccgaccgtg   360
ggtcaggtgg gtttgttggc gccggccctg tttatcctgc tgcgtctggt ccagggcatc   420
ttcgtgggcg gtgtcgtggc cagcacccat accatcggca ccgagagcgt gccgccgtcg   480
tggcgcggcg ccgtcagcgg tttggtgggc ggcggcggcg cgggcatcgg tgccttgctg   540
gcgagcatca cctacatggc catgaccgcc ctgttcccgg gcgaagcgtt tgacgcgtgg   600
ggttggcgct gcatgttctt ctcgggcatc attagctcgg tgctgggcct gttcatcttc   660
aatagcctgg aagagagccc cctgtggaaa cagctgcagg cggcgaaggg ccacgccgcc   720
ccggtggaga atccgctgcg tgtgattttc agccgccagt accgcggcgt gctgttcgtg   780
aacatcctgc tgaccgtggg cggtggcagc gcgtattacc tgaccagcgg ctacttgccc   840
accttcctga aagtcgtggt gaaggcccg gccggtgcgt cggccgccat tctgatggcc   900
agcagcgtcg gcgtgatcgt ggcgagcatc attgcgggcc acctgtcgac cctgatcggt   960
cgcaagcgcg ccttcttgct gatcggcgcg ctgaatgtgg tcctgctgcc gttgatctat  1020
cagcgcatgc cggccgcccc ggacgtgacc acgctgggca tctatgcggt ggccctggcc  1080
atgctgggca gcacgggctt tgcgcccatc ttgatcttcc tgaacgaacg cgtgtcgcac  1140
cagcatccgt gctatggcaa ctggccggtg atggagtatc gtttgtgcca ccgccgccac  1200
gacgccacct tcgccagcct gtgtgccgcc ccgccgcgtt tgccgaagtg ctggggttcg  1260
cgtcgtggcg tgaaggcgtt caccgccggc gccgccattg tgtggaacgc cccgttgggc  1320
gagtaa                                                             1326
```